United States Patent [19]

Braxton et al.

[11] Patent Number: 6,001,632
[45] Date of Patent: Dec. 14, 1999

[54] HUMAN PROTEIN DISULFIDE ISOMERASE

[75] Inventors: Scott Michael Braxton, San Mateo; Lynn E. Murry, Portola Valley, both of Calif.

[73] Assignee: Incyte Pharmaceuticals, Inc., Palo Alto, Calif.

[21] Appl. No.: 09/181,318

[22] Filed: Oct. 27, 1998

Related U.S. Application Data

[60] Division of application No. 08/650,275, May 16, 1996, Pat. No. 5,798,249, which is a continuation-in-part of application No. 08/649,740, May 15, 1996, abandoned.

[51] Int. Cl.$^6$ .............................. C12N 9/90; C12N 1/20; C12N 15/00; C07H 21/04
[52] U.S. Cl. ................. 435/233; 435/69.1; 435/252.3; 435/320.1; 530/350; 536/23.2
[58] Field of Search .................................. 435/233, 69.1, 435/252.3, 320.1; 530/350; 536/23.2

[56] References Cited

FOREIGN PATENT DOCUMENTS

| 0 277 563 A1 | 8/1988 | European Pat. Off. . |
| 0 509 841 A2 | 10/1992 | European Pat. Off. . |
| WO 94/20618 | 9/1994 | WIPO . |

OTHER PUBLICATIONS

Laboissiere, M., et al., "The Essential Function of Protein–disulfide Isomerase Is to Unscramble Non–native Disulfide Bonds," *The Journal of Biological Chemistry*, 270(47):28006–28009 (1995).
Tasanen, K., et al., "Promoter of the Gene for the Multifunctional Protein Disulfide Isomerase Polypeptide," *The Journal of Biological Chemistry*, 267 (16):11513–11519 (1992).
LaMantia, M., et al., "Glycosylation site binding protein and protein disulfide isomerase are identical and essential for cell viability in yeast," *Proc. Natl. Acad. Sci. USA*, 88:4453–4457 (1991).
Pihlajaniemi, T., et al., "Molecular cloning of the β–subunit of human prolyl 4–hydroxylase. This subunit and protein disulphide isomerase are products of the same gene," *The EMBO Journal*, 6(3):643–649 (1987).
Hayano, T., et al., "Molecular cloning of the cDNA encoding a novel protein disulfide isomerase–related protein (PDIR)," *FEBS Letters*, 372:210–214 (1995).
Wilson, R., et al., "2.2 Mb of contiguous nucleotide sequence from chromosome III of *C. elegans,*" *Nature*, 368:32–38 (1994) (GI 1086627).
Shorrosh, B., et al., "Molecular characterization and expression of an alfalfa protein with sequence similarity to mammalian ERp72, a glucose–regulated endoplasmic reticulum protein containing active site sequences of protein disulphide isomerase," *The Plant Journal*, 2(1)51–58 (1992) (GI 729442).
Hillier, L., et al. (GI 149007) GenBank Sequence Database (Accession N30487) National Center for Biotechnology Information, National Library of Medicine, Bethesda, Maryland 2084.

Edman, J., et al., "Sequence of protein disulphide isomerase and implications of its relationship to thioredoxin," *Letters to Nature*, 317:267–270 (1985).
Essex, D., et al., "Localization of Protein Disulfide Isomerase to the External Surface of the Platelet Plasma Membrane," *Blood*, 86(6)2168–2173 (1995).
Terada, K., et al., "Secretion, Surface Localization, Turnover, and Steady State Expression of Protein Disulfide Isomerase in Rat Hepatocytes," *The Journal of Biological Chemistry*, 270(35)20410–20416 (1995).
Marra, M et al., (GI 1284976) GenBank Sequence Database (Accession W10660), National Center for Biotechnology Information, National Library of Medicine, Bethesda, Maryland, 20894.
Fujiwara, T et al., (GI 968238) GenBank Sequence Database (Accession D58604), National Center for Biotechnology Information, National Library of Medicine, Bethesda, Maryland, 20894.
Ryser, HJP, et al., "Inhibition of human immunodeficiency virus infection by agents that interfere with thiol–disulfide interchange upon virus–receptor interaction" *Proc. Natl. Acad. Sci USA* 91:4559–4563 (1994).
Kaetzel, CS, et al., "Protein disulphide–isomerase from human placenta and rat liver: Purification and immunological characterization with monoclonal antibodies" *Biochem. J.* 241:39–47 (1987).
Morjana, NA et al., "Effect of Protein and Peptide Inhibitors on the Activity of Protein Disulfide Isomerase" *Biochemistry* 30:4985–4990 (1991).
Charnock–Jones, D., et al., Cloning, Expression and Genomic Organization of Human Placental Protein Disulfide Isomerase (Previously Identified as Phospholipase C Alpha), *Int. J. Biochem. Cell Biol.*, 28(1): 81–89 (1996).
McLaughlin, S.H. and R.B. Freedman, "Cloning and expression of active domains of human protein disulphide isomerase", *Biochemical Soc. Trans.*, 23: 69S (1995).
Parry, J.W.L., et al., "The expression in *E. coli* purification and isolated non–thioredoxin–like domains of human PDI", *Biochemical Soc. Trans.*, 23: 71S (1995).
Vuori, K. et al.,"Expression and Site–directed Mutagenesis of Human Protein Disulfide Isomerase in *Escherichia coli*", *J. Biol. Chem.*, 267(11): 7211–7214 (1992).

*Primary Examiner*—Robert A. Wax
*Assistant Examiner*—Tekchand Saidha
*Attorney, Agent, or Firm*—Incyte Pharmaceuticals Inc.

[57] ABSTRACT

The present invention provides a polynucleotide (pdih) the partial sequence for which was initially isolated from a lung cDNA library and which identifies and encodes a novel human protein disulfide isomerase (PDIH). The invention provides for genetically engineered expression vectors and host cells comprising the nucleic acid sequence encoding PDIH. The invention also provides for the use of purified PDIH and its agonists in the commercial production of recombinant proteins and in pharmaceutical compositions for the treatment of diseases associated with the abnormal expression of PDIH. Additionally, the invention provides for the use of antisense molecules to pdih or inhibitors of PDIH in pharmaceutical compositions for treatment of diseases. The invention also describes diagnostic assays which utilize diagnostic compositions comprising the polynucleotide, fragments or the complement thereof, which hybridize with the genomic sequence or the transcript of pdih, or anti-PDIH antibodies which specifically bind to the polypeptide, PDIH.

2 Claims, 13 Drawing Sheets

```
                                                                                    54
5' NAG GTG CCG CTG CCT GGA GAA TCC TCC GCT GCC GTC GNT CCC GGA GCC AGC CCT
        9            18           27           36           45

108
TTC CTA ACC CAA CCC AAN CCA GCC CAG TCC CAG CCG CNA GCG CCT GTC CCT GTC
        63           72           81           90           99

162
ACG GAC CCC AGC GTT ACC ATG CAT CCT GCC GTC TTC CTA TCC CTA CCC GAC CTC
       117          126          135          144          153
                             M   H   P   A   V   F   L   S   L   P   D   L

216
AGA TGC TCC CTT CTG CTG GTA ACT TGG GTT TTT ACT CCT GTA ACA ACT GAA
    R   C   S   L   L   L   V   T   W   V   F   T   P   V   T   T   E
       171          180          189          198          207

270
ATA ACA AGT CTT GCT ACA GAG AAT ATA GAT GAA ATT TTA AAC AAT GCT GAT GTT
    I   T   S   L   A   T   E   N   I   D   E   I   L   N   N   A   D   V
       225          234          243          252          261

324
GCT TTA GTA AAT TTT TAT GCT GAC TGG TGT CGT TTC AGT CAG ATG TTG CAT CCA
    A   L   V   N   F   Y   A   D   W   C   R   F   S   Q   M   L   H   P
       279          288          297          306          315

378
ATT TTT GAG GAA GCT TCC GAT GTC ATT AAG GAA GAA TTT CCA AAT GAA AAT CAA
    I   F   E   E   A   S   D   V   I   K   E   E   F   P   N   E   N   Q
       333          342          351          360          369
```

FIGURE 1A

```
      387       396       405       414       423       432
GTA GTG TTT GCC AGA GTT GAT TGT GAT CAG CAC TCT GAC ATA GCC CAG AGA TAC
 V   V   F   A   R   V   D   C   D   Q   H   S   D   I   A   Q   R   Y 441       450       459       468       477       486
AGG ATA AGC AAA TAC CCA ACC CTC AAA TTG TTT CGT AAT GGG ATG ATG ATG AAG
 R   I   S   K   Y   P   T   L   K   L   F   R   N   G   M   M   M   K 495       504       513       522       531       540
AGA GAA TAC AGG GGT CAG CGA TCA GTG AAA GCA GAT TTG GCA GAT TAC ATC AGG CAA
 R   E   Y   R   G   Q   R   S   V   K   A   D   L   A   D   Y   I   R   Q 549       558       567       576       585       594
CAA AAA AGT GAC CCC ATT CAA GAA ATH CGG GAC TTA GCA GAA ATC ACC ACT CTT
 Q   K   S   D   P   I   Q   E   I   R   D   L   A   E   I   T   T   L 603       612       621       630       639       648
GAT CGC AGC AAA AGA AAT ATC ATT GGA TAT TTK GAG CAA AAG GAC TCG GAC AAC
 D   R   S   K   R   N   I   I   G   Y   X   E   Q   K   D   S   D   N 657       666       675       684       693       702
TAT AGA GTT TTT GAA CGA GTA GCG AAT ATT TTG CAT GAT GAC TGT GCC TTT CTT
 Y   R   V   F   E   R   V   A   N   I   L   H   D   D   C   A   F   L 711       720       729       738       747       756
TCT GCA TTT GGG GAT GTT TCA AAA CCG GAA AGA TAT AGT GGC GAC AAC ATA ATC
 S   A   F   G   D   V   S   K   P   E   R   Y   S   G   D   N   I   I
```

FIGURE 1B

```
              765            774            783            792            801            810
TAC AAA CCA CCA GGG CAT TCT GCT CCG GAT ATG GTG TAC TTG GGA GCT ATG ACA
 Y   K   P   P   G   H   S   A   P   D   M   V   Y   L   G   A   M   T 819            828            837            846            855            864
AAT TTT GAT GTG ACT TAC AAT TGG ATT CAA GAT AAA TGT GTT CCT CTT GTC CGA
 N   F   D   V   T   Y   N   W   I   Q   D   K   C   V   P   L   V   R 873            882            891            900            909            918
GAA ATA ACA TTT GAA AAT GGA GAG TTG ACA GAA GAA GGA CTG CCT TTT CTC
 E   I   T   F   E   N   G   E   L   T   E   E   G   L   P   F   L 927            936            945            954            963            972
ATA CTC TTT CAC ATG AAA GAA GAT ACA GAA AGT TTA GAA ATA TTC CAG AAT GAA
 I   L   F   H   M   K   E   D   T   E   S   L   E   I   F   Q   N   E 981            990            999            1008           1017           1026
GTA GCT CGG CAA TTA ATA AGT GAA AAA GGT ACA ATA AAC TTT TTA CAT GCC GAT
 V   A   R   Q   L   I   S   E   K   G   T   I   N   F   L   H   A   D 1035           1044           1053           1062           1071           1080
TGT GAC AAA TTT AGA CAT CCT CTT CTG CAC ATA CAG AAA ACT CCA GCA GAT TGT
 C   D   K   F   R   H   P   L   L   H   I   Q   K   T   P   A   D   C 1089           1098           1107           1116           1125           1134
CCT GTA ATC GCT ATT GAC AGC TTT AGG CAT ATG TAT GTG TTT GGA GAC TTC AAA
 P   V   I   A   I   D   S   F   R   H   M   Y   V   F   G   D   F   K
```

FIGURE 1C

```
            1143        1152        1161        1170        1179       1188
       GAT GTA TTA ATT CCT GGA AAA CTC AAG CAA TTC GTA TTT GAC TTA CAT TCT GGA
        D   V   L   I   P   G   K   L   K   Q   F   V   F   D   L   H   S   G 1197        1206        1215        1224        1233       1242
       AAA CTG CAC AGA GAA TTC CAT CAT GGA CCT GAC CCA ACT GAT ACA GCC CCA GGA
        K   L   H   R   E   F   H   H   G   P   D   P   T   D   T   A   P   G 1251        1260        1269        1278        1287       1296
       GAG CAA GCC CAA GAT GTA GCA AGC AGT CCA CCT GAG AGC TCC TTC CAG AAA CTA
        E   Q   A   Q   D   V   A   S   S   P   P   E   S   S   F   Q   K   L 1305        1314        1323        1332        1341       1350
       GCA CCC AGT GAA TAT AGG TAT ACT CTA TTG AGG GAT CGA GAT GAG CTT TAA AAA
        A   P   S   E   Y   R   Y   T   L   L   R   D   R   D   E   L   *

1359        1368        1377        1386        1395       1404
       CTT GAA AAA CAG TTT GTA AGC CTT TCA ACA GCA TCA ACC TAC GTG GTG GAA 1413        1422        1431        1440        1449       1458
       ATA GTA AAC CTA TAT TTT CAT AAT TCT ATG TGT ATT TTT ATT TTG AAT AAA CAG 1467        1476        1485        1494
       AAA GAA ATT TTG GGG TTT TAT TTT TTT NTC CCC GGC  3'
```

CONSENSUS    +--------------------------------------------->
             +-----------|-----------|-----------|-----------|
             0          400         800        1200       1600
```

FIGURE 2

```
  1  MHPAVFLSLPDLRCSLLLV-TWVFTPVTTE-ITSLATEN                    aa 809200
  1  MFHEMFFYKKNQKTDLKKLV--VF-------                            GI 1086627
  1  MKMEMHQIWS--RIALASFAFAILFVSADDVVVLTEEN                     GI 729442

39  IDEILNNADVALVNFYADWCRFSQMLHPIFEEASDVIKEE                   aa 809200
 23  -------VAFCADWCPFSRRLKPIFEESARVFHQE                        GI 1086627
 39  FEKEVGHDKGALVEFYAPWCGHCKKLAPEYEKLPNSFKK-                   GI 729442

79  FPNENQVFARVDCDQHSDIAQRYRISKYPTLKLFRNGMM                    aa 809200
 51  NPQASAV-WAIVDSQRQADIGDKYFVNKYPTMKVFVNGEL                   GI 1086627
 78  ---AKSVLIAKVDCDEHKSVCSKYGVSGYPTIQWFPKGSL                   GI 729442

119  MKREYRGQRSVKALADYIRQQKSDPIQEIRDLAEIT-TLD                   aa 809200
 90  ITKEYRSTRSVEALTNFVKFQLSTAINEFSSQDLNQEMD                    GI 1086627
115  EPKKFEGPRTAESLAEFVNTEGGTNVKIATAPSHVV-VLT                   GI 729442

158  RSKRNIIGYXEQKDSDNYRVFERVANILHDDCAFLSA---                   aa 809200
130  KSKRNVVAWL-KKDGPEFANLKKVASILREDCSFWVPTDH                   GI 1086627
154  PETFNEVVLDGTKD----VLVEFYAPWCGHCKSLAPI---                   GI 729442

195  FGDVSKPERYSGDNIIYKPPGHSAPDMVYLGAMTNFDVTY                   aa 809200
169  FGTNDNKLS----FDPDSNEEAK----FTGNFNDYDFVK                    GI 1086627
187  YEKVAAVFKSEDDVVIANLDADK-----FRDLAEKYDVS-                   GI 729442
```

FIGURE 3A

```
235 NWIQDKCVPLVREITFENGEELTEEGLPFLILFHMKEDTE          aa 809200
203 QWVTDKCIPLVREVTFENVEELTEEGMPFLIYFRDPDNKT          GI 1086627
221 -------------------------GFPTLKFF--PKGNK          GI 729442

275 SLEIFQNEVARQLISEKGTINFLHADCDKFRHPLLHIQKT          aa 809200
243 TDKVFGEAVARELYDQRSAINPLLADGHKFAHPLKHLGKT          GI 1086627
234 AGEDYGG--GRDL---DDFVAFINEKSGTSRDAKGQLTSE          GI 729442

315 PADCPVIAIDSFRHMYVFGDFKDVLIPGKLKQFVFDLHSG          aa 809200
283 KEDLPVLAIDSFQHMYLFPDMTQMNIPGKLREFVMDLHSG          GI 1086627
269 AG------IVEDLDEL--VKEFVAANDEEKKAVFARIEEEV         GI 729442

355 KLHREFH-------HGPDPTDTAPGEQAQDV                   aa 809200
323 KLHKDFHENLDQRMIELAKAKAARGITDDHEAQAPSTRPI          GI 1086627
302 KKLEGSASRYGKIYLKVSKKYLEKGSDYAKNEIQRLERLL          GI 729442

379 ASSPPESSFQKLAPSEYRYTLLRDRDEL                      aa 809200
363 DTTPPPSVFKELKPSDKRYSIL-QKSEL                      GI 1086627
342 EKSISPAKADELTLKK---NILSTYA                        GI 729442
```

FIGURE 3B

HUMAN PROTEIN DISULFIDE ISOMERASE

CROSS-REFERENCE TO RELATED APPLICATIONS

This application is a divisional application of U.S. application Ser. No. 08/650,275, filed May 16, 1996, now U.S. Pat. No. 5,798,249 which is a continuation-in-part of U.S. application Ser. No. 08/649,740, filed May 15, 1996, now abandoned.

FIELD OF THE INVENTION

The present invention relates to nucleic acid and amino acid sequences of a novel human protein disulfide isomerase and to the use of these sequences in the diagnosis, study, prevention and treatment of disease.

BACKGROUND OF THE INVENTION

Cells contain a number of proteins known as molecular chaperones or foldases. These molecules catalyse the folding of newly synthesized proteins, prevent aggregation and improper glycosylation, and remove denatured proteins. Although they do not become part of the final structure, they are important in the assembly of proteins or their subunits into larger, more complex structures. In the absence of chaperones and foldases, misfolded proteins are quickly degraded by intracellular proteases.

The molecular chaperones include the heat shock proteins (particularly Hsp70) such as DnaK and binding protein (BiP). Both DnaK and BiP may be located in the cytoplasm where they bind to newly formed proteins as they are released from the ribosomal machinery. These chaperones prevent aggregation by binding to the "sticky" or hydrophobic surfaces of the protein molecule. The catalytic protein disulfide isomerase (PDI; also known as glycosylation site binding protein, GSBP) is a foldase (or shufflease; Laboissiere M C et al. (1995) J Biol Chem 270:28006–9) which is found in membrane-bound eukaryotic compartments such as the endoplasmic reticulum (ER). It facilitates disulfide bond exchange as well as correct glycosylation. Molecular chaperones and foldases disassociate from their protein substrates as soon as the protein has assumed its native conformation.

In prokaryotes such as *E. coli*, DnaK, an Hsp70 molecule, binds to partially folded cytoplasmic proteins and facilitates their folding. In *E. coli*, export of a partially folded protein may also be facilitated by molecular chaperone. Because protein folding is both a stoichometric and an energy requiring process, overexpression of recombinant proteins in prokaryotes commonly leads to aggregation of the protein and results in the formation of inclusion bodies.

Although a bacterial form of hsp70 is found in the mitochondria, BiP is a specialized eukaryotic Hsp70 which carries out its activities in the ER. BiP binds to hydrophobic portions of a nascent protein before the protein leaves the ribosome and hydrolyzes ATP to provide energy for the folding that allows the protein to attain its native conformation. Although the exact energy cost for protein folding is unknown, estimates range from 30–100 molecules per turnover event.

Foldases, such as PDI, are specialized enzymes which carry out rate-limiting covalent steps in protein folding. These enzymes are most abundant in cells actively synthesizing secreted proteins which are major components of the ER lumen (Tasanen K et al. (1992) J Biol Chem 267:11513–19) and may constitute 1–2% of eukaryotic cellular proteins. Although incubation of reduced unfolded proteins in buffers with defined ratios of oxidized and reduced thiols can lead to native conformation, the rate of folding is slow and the attainment of native conformation decreases proportionately to the size and number of cysteines in the protein. In contrast, PDI in the eukaryotic ER is much more efficient in carrying out the enzymatic pairing and oxidation of cysteines.

In general, disulfides are formed only in secretory compartments such as the ER or periplasmic space because the redox potential of the cytoplasm is unfavorable. The correct folding of proteins which contain disulfide bonds is also most likely to occur when the protein is expressed with an intact leader sequence which allows Its export into appropriate compartments for enzymatic processing by PDI.

LaMantia et al. (1994; Proc Natl Acad Sci 88:4453–57) first reported that PDI and GSBP were identical in yeast. Disruption of the gene in yeast experimentally resulted in a recessive lethal mutation demonstrating that PDI/GSBP activity is necessary for cell viability. Other molecules found in cells actively secreting proteins and closely related to PDI are the β subunit of the tetrameric prolyl 4-hydroxylass (Pihlajaniemi T et al. (1987) EMBO J 6:643–49), a component of the triglyceride transfer protein, and a thyroid hormone binding protein (cf. Hayano T and M Kikuchi (1995) FEBS Lett 372:210–214).

SUMMARY

The present invention relates to a novel human protein disulfide isomerase initially identified among the partial cDNAs from a lung library and to the use of the nucleic acid and amino acid sequences in the study, diagnosis, prevention and treatment of disease.

The human protein disulfide isomerase of the present invention was first identified in the partial cDNA, Incyte Clone 809200p, through a computer-generated search for amino acid sequence alignments. The consensus nucleic acid sequence, SEQ ID NO: 1, disclosed herein and designated in lower case, pdih, encodes the amino acid sequence, SEQ ID NO: 2, designated in upper case, PDIH. The present invention is based, in part, on the chemical and structural homology between PDIH, *Caenorhabditis elegans* thioredoxin (GI 1086627; Wilson et al. (1994) Nature 368:32–8), and alfalfa protein disulfide isomerase (GI729442; Shorrosh B S and R A Dixon (1995) Plant J 2:51–58).

PDIH has 39% identity to the *C. elegans* thioredoxin, and 16% identity to alfalfa protein disulfide isomerase. In addition, the hydrophobicity and isoelectric plots of these three molecules are very similar which indicates similar configuration and activity. The novel PDIH is 406 amino acids long and has a conserved ER retention signal, RDEL, at the 3' end of the peptide. It lacks potential glycosylation sites and the conserved CXXC residues and flanking residues of the known PDIs.

The nucleic acid sequence, oligonucleotides, fragments, portions or antisense molecules thereof, may be used in diagnostic assays of body fluids or biopsied tissues to detect the expression level of pdih. For example, pdih sequences designed from the consensus sequence (SEQ ID NO:1) or the overlapping sequences found in Incyte Clones 008697, 014106, 019812, 029425, 032387, 053124, 285763, 291250, 292789, 318606, 350290, 365690, 406416, 450935, 478027, 478085, 521643, 533824, 545675, 564725, 587535, 591297, 631328, 637955, 788789, 809200p, 812834, 835802, 881621, and 882286 (SEQ ID NOs: 5–34) can be used to detect the presence of the mRNA transcripts in a patient or to monitor the decrease in transcripts during treatment.

The present invention relates, in part, to the inclusion of the polynucleotide encoding PDIH in an expression vector which can be used to transform host cells or organisms. Such transgenic hosts are useful for the production of PDIH. Purified PDIH is also useful for the in vitro production and folding of recombinant, therapeutic human proteins. Addition of PDIH to the reaction mixture improves the yield of biologically active, therapeutic protein.

The nucleic acid sequence also provides for the design of antisense molecules useful in diminishing or eliminating expression of the genomic nucleotide sequence in platelets or hepatocytes individuals in which PDIH activity would ameliorate diseases such as athersosclersis and immunodeficiency diseases of the liver such as biliary cirrhosis, respectively.

The invention further provides diagnostic kits for the detection of naturally occurring PDIH. It provides for the use of purified PDIH as a positive control and to produce antibodies which can be used to quantitate the amount of PDIH in human body fluids or biopsied tissues. PDIH can also be used to identify agonists which induce the production of or prolong the lifespan of the PDIH molecule in vivo or in vitro. PDIH can be similarly used to screen for antagonists or inhibitors which bind PDIH and can be used to alter the activity of PDIH secreted by platelets or hepatocytes and contributing to atherosclerosis or immune problems of the liver, respectively. Such antagonists or inhibitors can be delivered into the vascular system or appropriate cell compartments to interact with PDIH and alter protein folding. Anti-PDIH antibodies are also useful for the inhibition of platelet and hepatocyte PDIH and to monitor PDIH activity during the course of treatment.

The invention comprises pharmaceutical compositions comprising the protein, antisense molecules capable of disrupting expression of the genomic sequence, and agonists, antibodies, antagonists or inhibitors of the disclosed protein. These compositions are useful for the prevention or treatment of conditions associated with abnormal expression of PDIH.

DESCRIPTION OF THE FIGURES

FIGS. 1A, 1B, 1C, and 1D displays the nucleic add sequence (SEQ ID NO:1) and deduced amino acid sequence (SEQ ID NO:2) of the human protein disulfide isomerase, PDIH. The alignment of the sequences was produced using MacDNAsis software (Hitachi Software Engineering Co Ltd).

FIG. 2 shows the electronic assembly diagram for Incyte Clone 809200 (SEQ ID NO:1) which used GI 1149007 (Hillier et al. (1996) WashU-Merck EST Project, unpublished) and 31 other partial cDNAs, Incyte Clones 008697, 014106, 019812, 029425, 032387, 053124, 285763, 291250, 292789, 318606, 350290, 365690, 406416, 450935, 478027, 478085, 521643, 533824, 545675, 564725, 587535, 591297, 631328, 637955, 788789, 809200p, 812834, 835802, 881621, and 882286 (SEQ ID NOs: 5–34). The consensus figure and sequence were assembled using the GELVIEW™ fragment assembly program from GCG (Madison Wis.).

FIGS. 3A and 3B shows the amino acid sequence alignments among PDIH (SEQ ID NO:2), C. elegans doxin reductase (GI 1086627; Wilson et al. (1994) Nature 368:32–8), and alfalfa protein disulfide isomerase (GI729442; Shorrosh B S and R A Dixon (1995) Plant J 2:51–58). Sequences wore aligned using the multisequence alignment program of DNAStar software (DNAStar Inc, Madison Wis.).

DETAILED DESCRIPTION OF THE INVENTION

Figure 4:
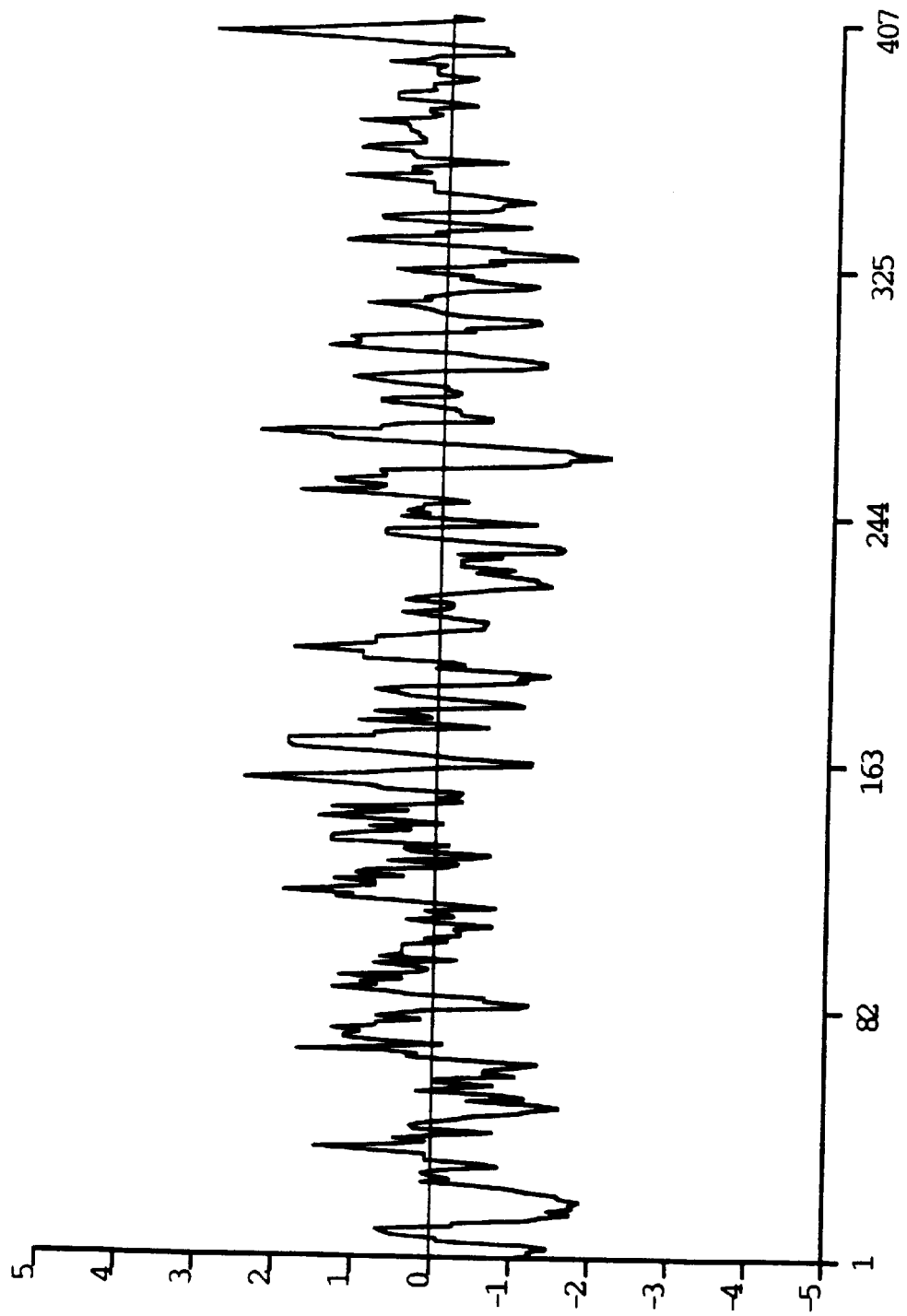
FIGS. 4–9 show the hydrophobicity (the X axis reflects amino acid position, and the negative Y axis, hydrophobicity) and isoelectric plots for PDIH (FIGS. 4 and 5), C. elegans thioredoxin reductase (FIGS. 6 and 7), and alfalfa PDI (FIGS. 8 and 9). These plots were generated using MacDNAsis software.

The present invention relates to a novel human protein disulfide isomerase initially identified among the partial cDNAs from a lung library and to the use of the nucleic acid and amino acid sequences in the study, diagnosis, prevention and treatment of disease.

The human protein disulfide isomerase of the present invention was first identified as a partial sequence in Incyte Clone 809200p through a computer-generated search for amino acid sequence alignments. The consensus nucleic acid sequence, SEQ ID NO: 1, disclosed herein and designated in lower case, pdih, encodes the amino acid sequence, SEQ ID NO: 2, designated in upper case, PDIH. The present invention is based, in part, on the chemical and structural homology between PDIH, Caenorhabditis elegans thioredoxin (GI 1086627; Wilson et al. (1994) Nature 368:32–8), and alfalfa protein disulfide isomerase (GI729442; Shorrosh B S and R A Dixon (1995) Plant J 2:51–58).

PDIH has 39% identity to the C. elegans thioredoxin, and 16% identity to alfalfa protein disulfide isomerase. In addition, the hydrophobicity and isoelectric plots of these three molecules are very similar. Two of the known human PDIs are the β subunit of the tetrameric prolyl 4-hydroxylase which is 503 amino acids long and has a signal peptide of 17 amino acids (Pihlajaniemi T et al, supra) and PDIR, the PDI-related protein from a human placental cDNA library which is 519 amino acids long (Hayano T and M Kikuchi, supra). The novel PDIH is 406 amino acids long, has a conserved ER retention signal, RDEL, at the 3' end, lacks potential glycosylation sites and the conserved CXXC residues of the alfalfa protein disulfide isomerase ($C_{58}GHC_{61}$ and $C_{178}GHC_{181}$), the β subunit prolyl 4-hydroxylase ($C_{36}XXC_{39}$ and $C_{80}XXC_{83}$) and the three Y/HAPW CGHCKXXXP motifs of PDIR.

The nucleic acid sequence, olignucleotides, fragments, portions or antisense molecules thereof, may be used in diagnostic assays of body fluids or biopsied tissues to detect the expression level of pdih. For example, pdih sequences designed from the consensus sequence (SEQ ID NO:1) or the overlapping sequences found in GI 1149007 and Incyte Clones 008697, 014106, 019812, 029425, 032387, 053124, 285763, 291250, 292789, 318606, 350290, 365690, 406416, 450935, 478027, 478085, 521643, 533824, 545675, 564725, 587535, 591297, 631328, 637955, 788789, 809200p, 812834, 835802, 881621, and 882286 (SEQ ID NOs: 5–34) can be used to detect the presence of the mRNA transcripts in a patient or to monitor the decrease in transcripts during treatment.

The present invention relates, in part, to the inclusion of the polynucleotide encoding PDIH in an expression vector which can be used to transform host cells or organisms. Such transgenic hosts are useful for the production of PDIH. Edman et al. (1995; Nature 317:267–70) reported that rat PDI is useful for the in vitro production and folding of recombinant human proteins. Likewise, purified PDIH is also commercially useful for the production and folding of recombinant, therapeutic human proteins such as tissue plasminogen activator (tPA).

The nucleic acid sequence also provides for the design of antisense molecules useful in diminishing or eliminating expression of the genomic nucleotide sequence in platelets or hepatocytes. PDIH activity is implicated in atherosclerosis and where the stress-induced, secretion of PDIH can cause tissue destruction in the vascular system (Essex D W et al. (1995) Blood 86:2168–73) and liver (Terada K et al. (1995) J Biol Chem 270:20410–6), respectively.

The invention further provides diagnostic kits for the detection of naturally occurring PDIH. It provides for the use of purified PDIH as a positive control and to produce antibodies which can be used to quantitate the amount of PDIH in human body fluids or biopsied tissues. PDIH can also be used to identify agonists which induce the production of or prolong the lifespan of the PDIH molecule in vivo or in vitro. PDIH can be similarly used to screen for antagonists or inhibitors which bind PDIH. Such antagonists or inhibitors can be delivered into the vascular system or appropriate cell compartments to interact with PDIH and alter protein folding. Anti-PDIH antibodies are also useful for the inhibition of platelet and hepatocyte PDIH and to monitor PDIH activity during the course of treatment.

The invention comprises pharmaceutical compositions comprising the protein, antisense molecules capable of disrupting expression of the native gene, and agonists, antibodies, antagonists or inhibitors of the disclosed protein. These compositions are useful for the prevention or treatment of conditions associated with abnormal expression of PDIH such as atherosclerosis.

The nucleotide sequences encoding PDIH (or its complement) have numerous applications in techniques known to those skilled in the art of molecular biology. These techniques include use as hybridization probes, use as oligomers for PCR, use for chromosome and gene mapping, use in the recombinant production of PDIH, and use in generation of antisense DNA or RNA, their chemical analogs and the like. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

It will be appreciated by those skilled in the art that as a result of the degeneracy of the genetic code, a multitude of PDIH-encoding nucleotide sequences, some bearing minimal homology to the nucleotide sequences of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring PDIH, and all such variations are to be considered as being specifically disclosed.

Although nucleotide sequences which encode PDIH and its variants are preferably capable of hybridizing to the nucleotide sequence of the naturally occurring pdih under appropriately selected conditions of stringency, it may be advantageous to produce nucleotide sequences encoding PDIH or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding PDIH and its derivatives without altering the encoded amino acid sequences include the production of RNA transcripts having more desirable properties, such as a greater half-life, than transcripts produced from the naturally occurring sequence.

The nucleotide sequences encoding PDIH may be joined to a variety of other nucleotide sequences by means of well established recombinant DNA techniques (cf Sambrook J et al. (1989) *Molecular Cloning: A Laboratory Manual*, Cold Spring Harbor Laboratory, Cold Spring Harbor N.Y.). Useful nucleotide sequences for joining to pdih include an assortment of cloning vectors, e.g., plasmids, cosmids, lambda phage derivatives, phagemids, and the like, that are well known in the art. Vectors of interest include expression vectors, replication vectors, probe generation vectors, and sequencing vectors. In general, vectors of interest will contain an origin of replication functional in at least one organism, convenient restriction endonuclease sensitive sites, and selectable markers for the host cell.

Another aspect of the subject invention is to provide for pdih specific nucleic acid hybridization probes capable of hybridizing with naturally occurring nucleotide sequences encoding PDIH. Such probes may also be used for the detection of related inhibitor encoding sequences and should preferably contain at least 50% of the nucleotides from any of these PDIH encoding sequences. The hybridization probes of the subject invention may be derived from the nucleotide sequence of the SEQ ID NOs:1 and 5–34 or from genomic sequence including promoter, enhancer elements and introns of the naturally occurring pdih. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

PCR as described in U.S. Pat. Nos 4,683,195 and 4,965,188 provides additional uses for oligonucleotides based upon the nucleotide sequences which encode PDIH. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for pdih DNAs include the cloning of nucleic acid sequences encoding PDIH or PDIH derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding a PDIH and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a pdih sequence or any portion thereof.

The nucleotide sequences may be used to construct an assay to detect activation or induction of pdih due to inflammation or disease. The nucleotide sequence may be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with the sample, indicating the presence of the inflammation and/or disease.

The nucleotide sequences for pdih may be used to construct hybridization probes for mapping their respective genomic sequences. The nudeotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a pdih on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

The nucleotide sequence encoding PDIH may be used to produce purified PDIH using well known methods of recombinant DNA technology. Among the many publications that teach methods for the expression of genes after they have been isolated is Goeddel (1990) Gene Expression Technology, Methods and Enzymology, Vol 185, Academic Press, San Diego. PDIH may be expressed in a variety of host cells, either prokaryotic or eukaryotic. Host cells may be from the same species from which a particular pdih nucleotide sequence was isolated or from a different species. Advantages of producing PDIH by recombinant DNA technology include obtaining adequate amounts of the protein for purification and the availability of simplified purification procedures.

Cells transformed with DNA encoding PDIH may be cultured under conditions suitable for the expression of PDIHs and recovery of the protein. PDIH produced by a recombinant cell may be secreted, contained intracellularly, or inserted into a membrane depending on the particular genetic construction used. In general, it is more convenient to prepare recombinant proteins In secreted form. Purification steps vary with the production process, the host organism and the particular protein produced.

In addition to recombinant production, fragments of PDIH may be produced by direct peptide synthesis using solid-phase techniques (cf Stewart et al (1969) Solid-Phase Peptide Synthesis, W H Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Various fragments of PDIH may be chemically synthesized separately and combined using chemical methods to produce the full length molecule.

PDIH for antibody induction does not require biological activity; however, the protein fragment, or oligopeptide must be immunogenic. Peptides used to induce specific antibodies may have an amino acid sequence consisting of at least five amino acids, preferably at least 10 amino acids. They should mimic a portion of the amino acid sequence of the natural protein and may contain the entire amino acid sequence of a small, naturally occurring molecule. Short stretches of PDIH amino acids may be fused with those of another protein such as keyhole limpet hemocyanin and antibody produced against the chimeric molecule.

Antibodies specific for PDIH may be produced by inoculation of an appropriate animal with the polypeptide or an antigenic fragment. An antibody is specific for the particular PDIH if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R et al (1989) PNAS 86:3833–3837, or Huse W D et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding PDIH.

An additional embodiment of the subject invention is the use of PDIH specific antibodies, as bioactive agents to treat conditions associated with secreted PDIH activity.

Bioactive compositions comprising agonists or antagonists of PDIH may be administered in a suitable therapeutic dose determined by any of several methodologies including clinical studio on mammalian species to determine maximum tolerable dose and on normal human subjects to determine safe dosage. Additionally, the bioactive agent may be complexed with a variety of well established compounds or compositions which enhance stability or pharmacological properties such as half-life. It is contemplated that a therapeutic, bioactive composition may be delivered into the ER by a liposome or other appropriate artificial vesicle.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to an oligopeptide, peptide, polypeptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

As used herein, PDIH refers to the amino acid sequence of PDIH from any species, particularly mammalian, including bovine, ovine, porcine, murine, equine, and preferably human, in a naturally occurring form or from any source whether natural, synthetic, semi-synthetic or recombinant. As used herein, "naturally occurring" refers to an amino acid sequence which is found in nature.

The present invention also encompasses PDIH variants. A preferred PDIH variant is one having at least 80% amino acid sequence similarity, a more preferred PDIH variant is one having at least 90% amino acid sequence similarity and a most preferred PDIH variant is one having at least 95% amino acid sequence similarity to the PDIH amino acid sequence (SEQ ID NO:2). A "variant" of PDIH may have an amino acid sequence that is different by one or more amino acid "substitutions".

The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to a PDIH having structural, regulatory or biochemical functions of the naturally occurring PDIH. Likewise, "immunologically active" defines the capability of the natural, recombinant or synthetic PDIH, or any oligopeptide thereof, to induce a specific immune response in appropriate animals or cells and to bind with specific antibodies.

The term "derivative" as used herein refers to the chemical modification of a pdih or the encoded PDIH. Illustrative of such modifications would be replacement of hydrogen by an alkyl, acyl, or amino group. A PDIH derivative would encode a polypeptide which retains essential biological characteristics of natural PDIH.

As used herein, the term "purified" refers to molecules, either nucleic or amino acid sequences, that are removed from their natural environment and isolated or separated from at least one other component with which they are naturally associated.

The PDIH Coding Sequences

The nucleic acid and deduced amino acid sequences of PDIH are shown in FIGS. 1A, 1B, 1C, and 1D. In accordance with the invention, any nucleic acid sequence which encodes the amino acid sequence of PDIH can be used to generate recombinant molecules which express PDIH. In a specific embodiment described herein, the sequence for pdih was first isolated as Incyte Clone 809200 from a lung cDNA library (LUNGNOT04).

Methods for DNA sequencing are well known in the art and employ such enzymes as the Kienow fragment of DNA polymerase I, Sequenase® (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.).

Methods to extend the DNA from an oligonucleotide primer annealed to the DNA template of interest have been developed for both single-stranded and doublstranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

The quality of any particular cDNA library may be determined by performing a pilot scale analysis of the cDNAs and checking for percentages of clones containing vector, lambda or *E. coli* DNA, mitochondrial or repetitive DNA, and clones with exact or homologous matches to sequences in public databases.

Extending the Polynucleotide Sequence

The polynucleotide sequence of pdih may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc. Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker J D et al (1991; Nucleic Acids Res 19:3055–60), teach walking PCR, a method for targeted gene walking which permits retrieval of unknown sequence. Promoter-Finder™ a new kit available from Clontech (Palo Alto Calif.) uses PCR, nested primers and PromoterFinder libraries to walk in genomic DNA. This process avoids the need to screen libraries and is useful in finding intron/exon junctions.

Another PCR method employs XL-PCR™ (Perkin Elmer) to amplify and extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode PDIH, fragments of the polypeptide, fusion proteins or functional equivalents thereof may be used in recombinant DNA molecules that direct the expression of PDIH in appropriate host cells. Due to the inherent degeneracy of the genetic code, other DNA sequences which encode substantially the same or a functionally equivalent amino acid sequence, may be used to clone and express PDIH. As will be understood by those of skill in the art, it may be advantageous to produce PDIH-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of PDIH expression or to produce recombinant RNA transcripts having desirable properties, such as a longer half-life, than transcripts produced from naturally occurring sequence.

Also included within the scope of the present invention are polynudeotide sequences that are capable of hybridizing to the nucleotide sequence of FIGS. 1A, 1B, 1C, and 1D under various conditions of stringency. Hybridization conditions are based on the melting temperature (Tm) of the nucleic acid binding complex or probe, as taught in Berger and Kimmel (1987, *Guide to Molecular Cloning Techniques*, Methods in Enzymology, Vol 152, Academic Press, San Diego Calif.) incorporated herein by reference, and confer may be used at a defined "stringency" as explained below.

"Maximum stringency" typically occurs at about Tm–5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Hybridization as used herein is differentiated from the process of amplification as carried out in the polymerase chain reaction technologies described in Dieffenbach C W and G S Dveksler (1995, *PCR Primer, a Laboratory Manual*, Cold Spring Harbor Press, Plainview N.Y.) and incorporated herein by reference.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring pdih.

A "substitution" results from the replacement of one or more nucleotides or amino acids by different-nucleotides or amino acids, respectively.

Altered pdih nudeic acid sequences which may be used in accordance with the invention include deletions, Insertions or substitutions of different nucleotides resulting in a polynucleotide that encodes the same or a functionally equivalent PDIH. The protein may also show deletions, insertions or substitutions of amino acid residues which produce a silent change and result in a functionally equivalent PDIH. Deliberate amino acid substitutions may be made on the basis of similarity in polarity, charge, solubility, hydrophobicity, hydrophilicity, and/or the amphipathic nature of the residues as long as the biological activity of PDIH is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of pdih. As used herein, an "allele" or "allelic sequence" is an alternative form of pdih. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

The nucleotide sequences of the present invention can be engineered in order to after a pdih coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant pdih sequence may be ligated to a heterologous sequence to encode a fusion protein. For example, for screening of peptide libraries for inhibitors of PDIH activity, it may be useful to encode a chimeric PDIH protein that is recognized by a commercially available antibody. A fusion protein may also be engineered to contain a cleavage site located between a PDIH sequence and the heterologous protein sequence, so that the PDIH may be cleaved and purified away from the heterologous moiety.

In an alternate embodiment of the invention, the coding sequence of pdih could be synthesized, whole or in part, using chemical methods well known in the art (see Caruthers M H et al (1980) Nuc Acids Res Symp Ser 215–23, Hom T et al(1980) Nuc Acids Res Symp Ser 225–32, etc). Alternatively, the protein itself could be produced using chemical methods to synthesize a PDIH amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be purified by preparative high performance liquid chromatography (eg, Creighton (1983) *Proteins, Structures and Molecular Principles*, W H Freeman and Co, New York N.Y.). The composition of the synthetic peptides may be confirmed by amino acid analysis or sequencing (eg, the Edman degradation procedure; Creighton, supra). Additionally the amino acid sequence of PDIH, or any part thereof, may be altered during direct synthesis and/or combined using chemical methods with sequences from other proteins, or any part thereof, to produce a variant polypeptide.

Expression Systems

In order to express a biologically active PDIH, the nucleotide sequence encoding PDIH or its functional equivalent, is inserted into an appropriate expression vector, ie, a vector which contains the necessary elements for the transcription and translation of the inserted coding sequence.

Methods which are well known to those skilled in the art can be used to construct expression vectors containing a PDIH coding sequence and appropriate transcriptional or translational controls. These methods include in vitro recombinant DNA techniques, synthetic techniques and in vivo recombination or genetic recombination. Such techniques are described in Maniatis et al (1989) *Molecular Cloning, A Laboratory Manual*, Cold Spring Harbor Press, Plainview N.Y. and Ausubel F M et al. (1989) *Current Protocols in Molecular Biology*, John Wiley & Sons, New York N.Y.

A variety of expression vector/host systems may be utilized to contain and express a pdih coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which Interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) or pSport1(Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of pdih, vectors based on SV40 or EBV may be used with an appropriate selectable marker.

In bacterial systems, a number of expression vectors may be selected depending upon the use intended for PDIH. For example, when large quantities of PDIH are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the pdih coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding PDIH may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Yearbook of Science and Technology (1992) McGraw Hill New York N.Y., pp 191–196 or Weissbach and Weissbach (1988) Methods for Plant Molecular Biology, Academic Press, New York N.Y., pp 421–463.

An alternative expression system which could be used to express pdih is an insect system. In one such system, *Autographa californica* nuclear polyhedrosis virus (AcNPV) is used as a vector to express foreign genes in *Spodoptera frugiperda* cells or in Trichoplusia larvae. The pdih coding sequence may be cloned into a nonessential region of the virus such as the polyhedrin gene, and placed under control of the polyhedrin promoter. Successful insertion of pdih will render the polyhedrin gene inactive and produce recombinant virus lacking coat protein coat. The recombinant viruses are then used to infect *S. frugiperda* cells or Trichoplusia larvae in which PDIH is expressed (Smith et al (1983) J Virol 46:584; Engelhard E K et al (1994) Proc Nat Aced Sci 91:3224–7).

In mammalian host cells, a number of viral-based expression systems may be utilized. In cases where an adenovirus is used as an expression vector, a pdih coding sequence may be ligated into an adenovirus transcription/translation complex consisting of the late promoter and tripartite leader sequence. Insertion in a nonessential E1 or E3 region of the viral genome will result in a viable virus capable of expressing PDIH in infected host cells. (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a pdih sequence. These signals include the ATG initiation codon and adjacent sequences. In cases where pdih, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, W138, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express pdih may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the pdih is inserted within a marker gene sequence, recombinant cells containing pdih can be identified by the absence of marker gene function. Alternatively, a marker gene can be placed in tandem with a PDIH sequence under the control of a single promoter. Expression of the marker gene in response to induction or selection usually indicates expression of the tandem pdih as well.

Alternatively, host cells which contain the coding sequence for pdih and express PDIH may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the pdih polynucleotide sequence can be detected by DNA-DNA or DNA-RNA hybridization or amplification using probes, portions or fragments of pdih. Nucleic acid amplification based assays involve the use of oligonucleotides or oligomers based on the pdih sequence to detect transformants containing pdih DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of PDIH, using either polyclonal or monoclonal antibodies specific for the protein are known in the art. Examples include eyzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on PDIH is preferred, but a competitive binding assay may be employed. These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to pdih include oligolabeling, nick translation, end-labeling or PCR amplification using a labeled nucleotide. Alternatively, the pdih sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of PDIH

Host cells transformed with a pdih nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing pdih can be designed with signal sequences which direct secretion of PDIH through a prokaryotic or eukaryotic cell membrane. Other recombinant constructions may join pdih to nucleotide sequence encoding a polypeptide domain which will facilitate purification of soluble proteins (Kroll D J et al (1993) DNA Cell Biol 12:441–53; cf discussion of vectors infra containing fusion proteins).

PDIH may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and PDIH is useful to facilitate purification.

Uses of PDIH

Figure 5:
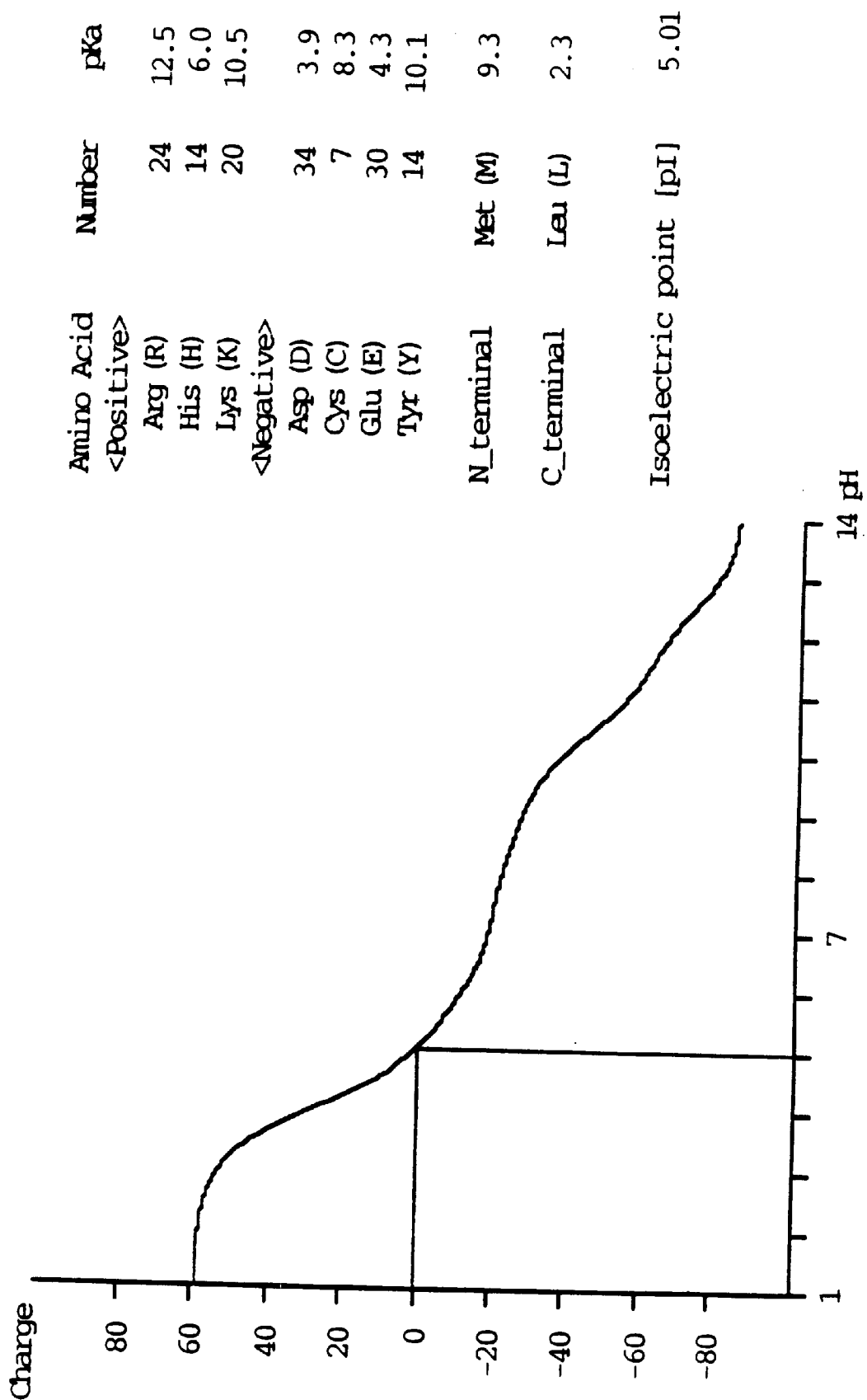
Figure 6:
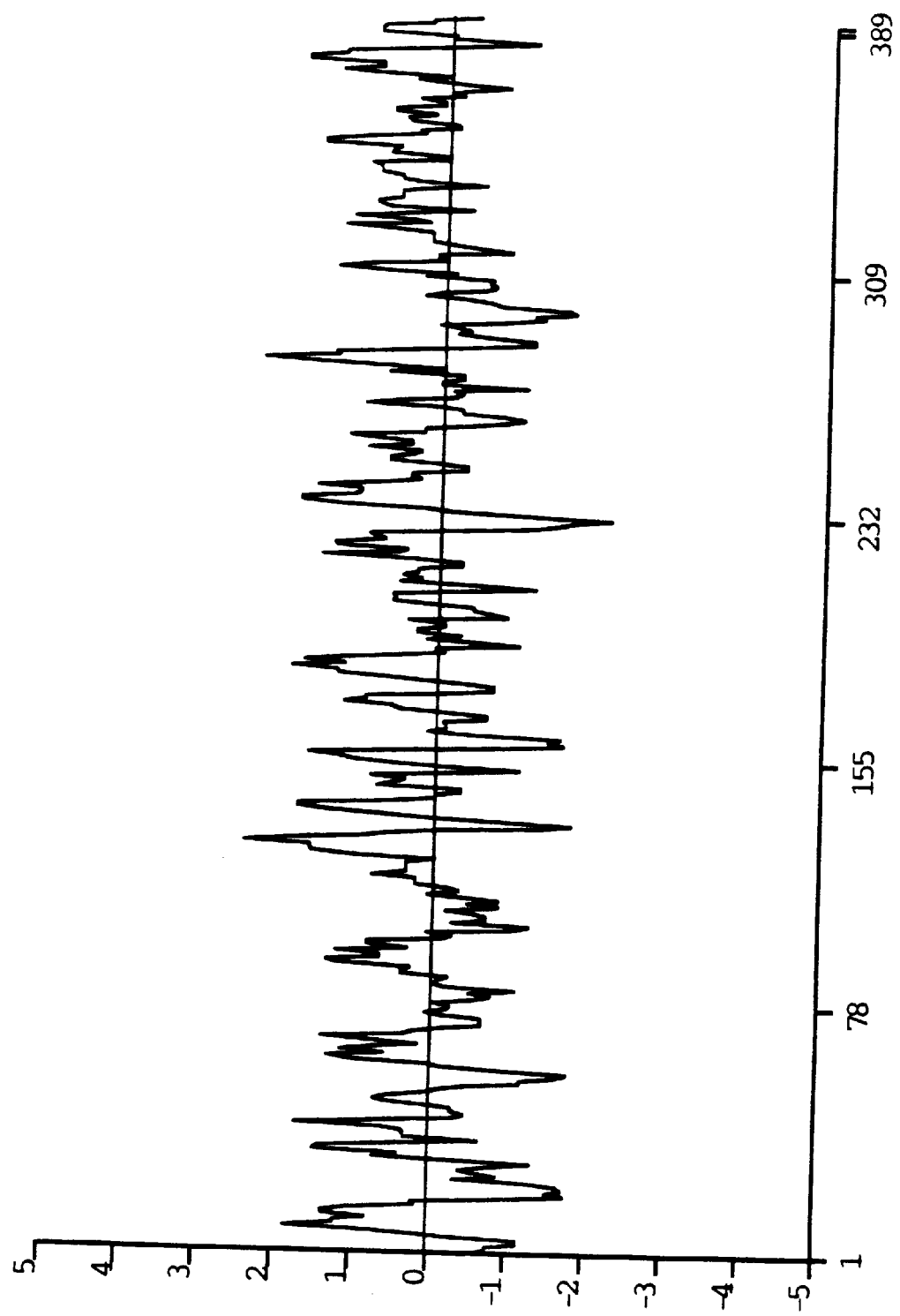
Figure 7:
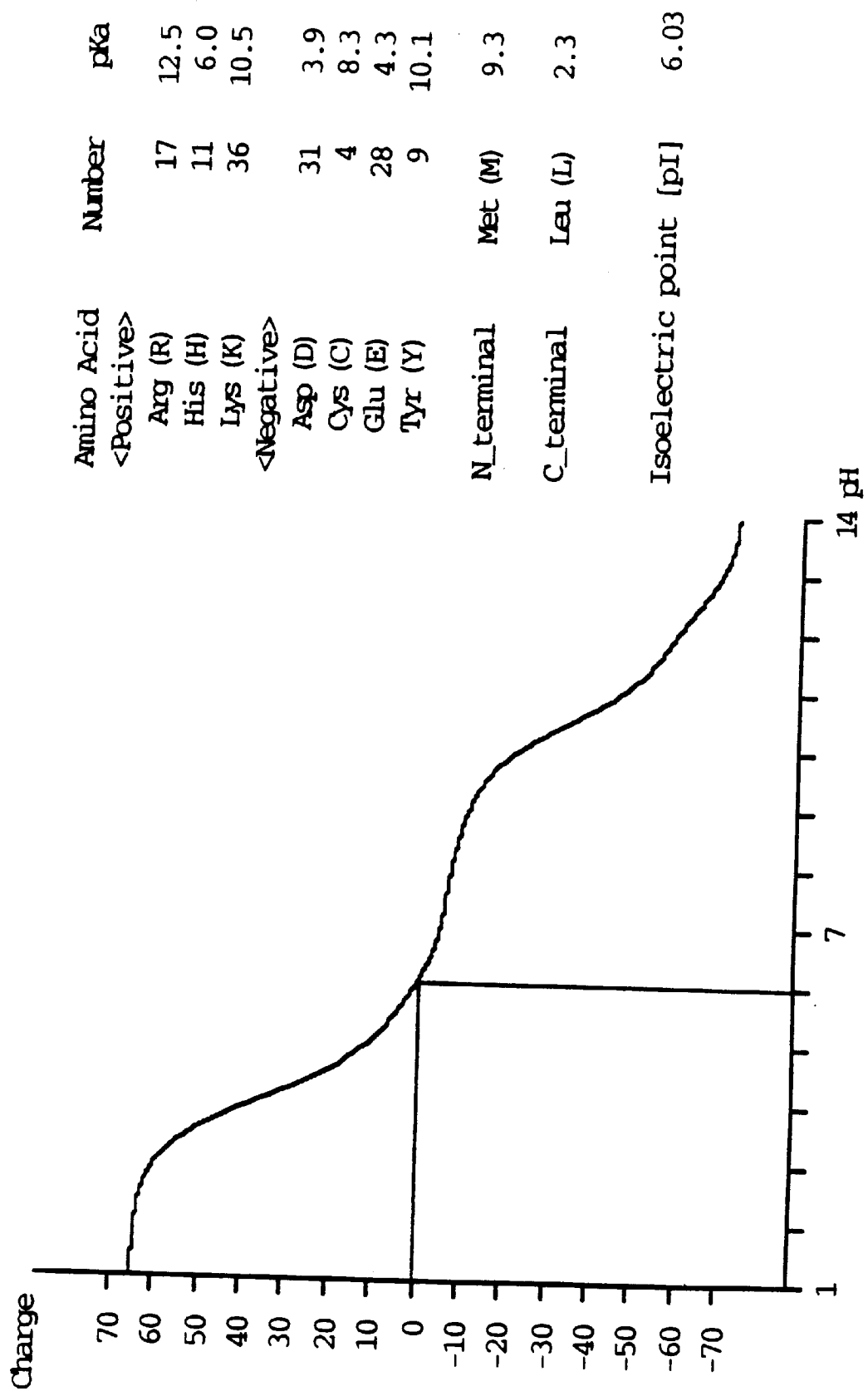
Figure 8:
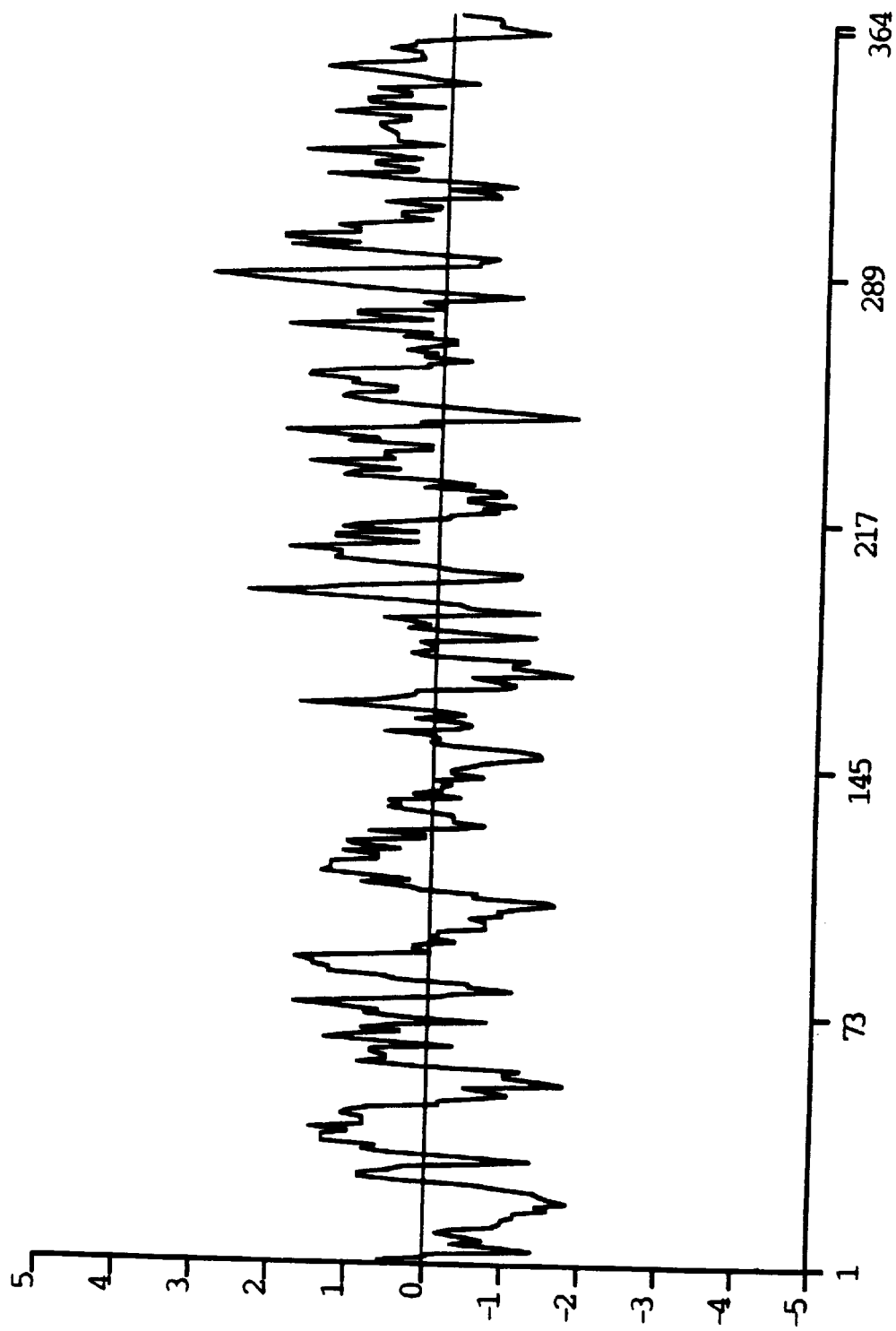
Figure 9:
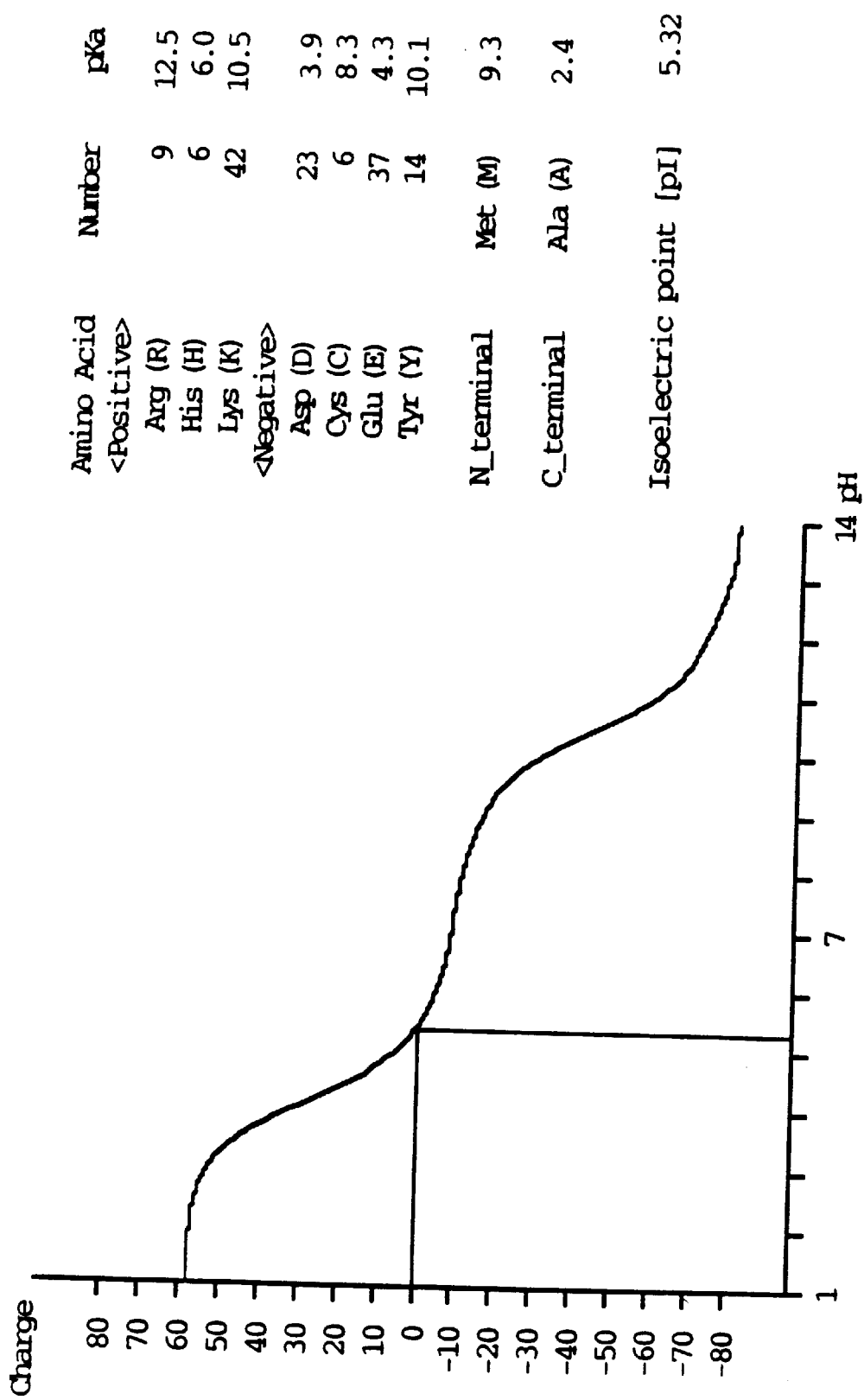

The rationale for industrial use of the nucleotide and peptide sequences disclosed herein is based on the chemical and structural homology among the novel PDIH, *C. elegans* thioredoxin, and alfalfa protein disulfide isomerase as shown in FIGS. 2–9.

The nucleic acid sequence (SEQ ID NO:1) can be placed in an expression vector which can be used to transform host cells or organisms. Such transgenic hosts are useful in two ways: 1) for the in vivo production and correct folding (in the ER or periplasmic space) of recombinant human proteins of commercial interest, and 2) for the production, secretion and purification of PDIH itself. Purified PDIH is then used in in vitro translation systems to obtain correctly folded and commercially relevant recombinant proteins such as tPA (cf Edman et al. (1995; Nature 317:267–70).

The nucleic acid sequence can also be used to design antisense molecules for diminishing or eliminating expression of the genomic nucleotide sequence in platelets or hepatocytes. These antisense sequences can be delivered to blood or liver cells in liposomes or other artificial vesicles to lessen pdih expression and reduce the secretion of PDIH and the tissue destruction attributed to the PDIH.

The invention further provides diagnostic kits for the detection of naturally occurring PDIH. It provides for the use of purified PDIH both as a positive control and to produce antibodies which can be used to quantitate the amount of PDIH in human body fluids or biopsied tissues and to monitor PDIH activity during the course of treatment.

PDIH can also be used to identify agonists which induce the production of or prolong the lifespan of the PDIH molecule in vivo or in vitro. PDIH can be similarly used to screen for antagonists or inhibitors which bind PDIH. Such antagonists or inhibitors can be delivered into the vascular system or appropriate cell compartments to interact with PDIH and alter protein folding. Antibodies antagonists and inhibitors are used to lessen the tissue destruction caused by the PDIH secreted platelets and hepatocytes.

The invention comprises pharmaceutical compositions comprising the protein, antisense molecules capable of disrupting expression of the genomic sequence, and agonists, antibodies, antagonists or inhibitors of the disclosed protein. These compositions are useful for the prevention or treatment of conditions associated with abnormal expression of PDIH. Conditions which were either mentioned in the literature or are associated with libraries from tissues in which partial pdih sequences were expressed (also shown in the Sequence ID listing) include atherosclerosis, anemias, asthma, systemic lupus, myasthenia gravis, diabetes mellitus, glomerulonephritis, atherosclerosis, rheumatoid and osteoarthritis, and biliary cirrhosis.

PDIH Antibodies

Procedures well known in the art can be used for the production of antibodies to PDIH. Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

For the production of antibodies, various hosts including goats, rabbits, rats, mice, etc may be immunized by injection with PDIH or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to PDIH may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce PDIH-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for PDIH may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W D et al (1989) Science 256:1275–1281).

PDIH-specific antibodies are useful for the diagnosis of conditions and diseases associated with expression of PDIH. A variety of protocols for competitive binding or immunoradiometric assays using either polyclonal or monoclonal antibodies with established specificities are well known in the art. Such immunoassays typically involve the formation of complexes between PDIH and its specific antibody and the measurement of complex formation. A two-site, monoclonal-based immunoassay utilizing monoclonal antibodies reactive to two noninterfering epitopes on a specific PDIH protein is preferred, but a competitive binding assay may also be employed. These assays are described in Maddox D E et al (1983, J Exp Med 158:1211).

Diagnostic Assays Using PDIH Specific Antibodies

Particular PDIH antibodies are useful for the diagnosis of conditions or diseases characterized by expression of PDIH or in assays to monitor patients being treated with PDIH, agonists or inhibitors. Diagnostic assays for PDIH include methods utilizing the antibody and a label to detect PDIH in human body fluids or extracts of cells or tissues. The polypeptides and antibodies of the present Invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring PDIH, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on PDIH is preferred, but a competitive binding assay may be employed. These assays are described, among other places, in Maddox, D E et al (1983, J Exp Med 158:1211).

In order to provide a basis for diagnosis, normal or standard values for PDIH expression must be established. This is accomplished by combining body fluids or cell extracts taken from normal subjects, either animal or human, with antibody to PDIH under conditions suitable for complex formation which are well known in the art. The amount of standard complex formation may be quantified by comparing various artificial membranes containing known quantities of PDIH with both control and disease samples from biopsied tissues. Then, standard values obtained from normal samples may be compared with values obtained from samples from subjects potentially affected by disease. Deviation between standard and subject values establishes the presence of disease state.

Drug Screening

PDIH, its catalytic or immunogenic fragments or oligopeptides, can be used for screening therapeutic compounds in any of a variety of drug screening techniques. The fragment employed in such a test may be free in solution, affixed to a solid support, borne on a cell surface, or located intracellularly. The formation of binding complexes, between PDIH and the agent being tested, may be measured.

Another technique for drug screening which provides for high throughput screening of compounds having suitable binding affinity to the PDIH is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of PDIH and washed. Bound PDIH Is then detected by methods well known in the art. Purified PDIH can also be coated directly onto plates for use in the aforementioned drug screening techniques. Afternatively, non-neutralizing antibodies can be used to capture the peptide and immobilize it on a solid support.

This invention also contemplates the use of competitive drug screening assays in which neutralizing antibodies capable of binding PDIH specifically compete with a test compound for binding PDIH. In this manner, the antibodies can be used to detect the presence of any peptide which shares one or more antigenic determinants with PDIH.

Uses of the Polynucleotide Encoding PDIH

A polynucleotide, pdih, or any part thereof, may be used for diagnostic and/or therapeutic purposes. For diagnostic purposes, the pdih of this invention may be used to detect and quantitate gene expression in biopsied tissues in which expression of PDIH may be implicated. The diagnostic assay is useful to distinguish between absence, presence, and excess expression of pdih and to monitor regulation of pdih levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding PDIH or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring pdih, alleles or related sequences.

Diagnostics

Polynucleotide sequences encoding PDIH may be used for the diagnosis of conditions or diseases with which the expression of PDIH is associated. For example, polynucleotide sequences encoding PDIH may be used in hybridization or PCR assays of fluids or tissues from biopsies to detect pdih expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

Such assays may be also be used to evaluate the efficacy of a particular therapeutic treatment regime in animal studies, in clinical trials, or in monitoring the treatment of an individual patient. In order to provide a basis for the diagnosis of disease, a normal or standard profile for pdih expression must be established. This is accomplished by combining body fluids or cell extracts taken from normal subjects, either animal or human, with pdih, or a portion thereof, under conditions suitable for hybridization or amplification. Standard hybridization may be quantified by comparing the values obtained for normal subjects with a dilution series of pdih run in the same experiment where a known amount of purified pdih is used. Standard values obtained from normal samples may be compared with values obtained from samples from patients affected by pdih-associated diseases. Deviation between standard and subject values establishes the presence of disease.

Once disease is established, a therapeutic agent is administered; and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195 and 4,965,188 provides additional uses for oligonucleotides based upon the pdih sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection andlor quantitation of closely related DNA or RNA sequences.

Additionally, methods to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitaton of multiple samples may be speeded up by running the assay in an ELISA format where the oligomer of interest is presented in various dilutions and a spectrophotometric or colorimetric response gives rapid quantitation. For example, the presence of pdih in extracts of biopsied tissues may indicate the onset of cancer. A definitive diagnosis of this type may allow health professionals to begin aggressive treatment and prevent further worsening of the condition. Similarly, further assays can be used to monitor the progress of a patient during treatment.

Therapeutics

The polynucleotide disclosed herein may be useful in the treatment of conditions associated with the libraries (shown in the Sequence ID Listing) which contained partial pdih sequences. These include atherosclerosis, anemias, asthma, systemic lupus, myasthenia gravis, diabetes mellitus, glomerulonephritis, rheumatoid and osteoarthritis, and biliary cirrhosis. Therefore, interfering with pdih transcription or translation, for example, by administration of a vector containing and expressing a pdih-binding antisense molecule, provides a means to moderate the amount of PDIH secreted by platelets which would contribute to atherosclerosis.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antipdih. See, for example, the techniques described in Maniatis et al (supra) and Ausubel et al (supra).

The polynucleotides comprising full length cDNA sequence and/or its regulatory elements enable researchers to use pdih as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding PDIH can be turned off by transfecting a cell or tissue with expression vectors which express high levels of the desired fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of pdih, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al. (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of pdih.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding PDIH. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences for pdih disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for pdih can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al. (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention comprises pharmaceutical compositions which may comprise nucleotides, proteins, antibodies, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used In the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of PDIH, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that inhibitors of PDIH can be delivered in a suitable formulation to block the tissue destruction associated with secretion of PDIH by hepatocytes (Terada et al, supra). Such administration of identified inhibitors should also ameliorate the effects of secretion of PDIH by hepatocytes and help treat immune system-associated diseases such as rheumatoid arthritis.

The examples below are provided to illustrate the subject invention and are not included for the purpose of limiting the invention.

EXAMPLES

I LUNGNOT04 cDNA Library Construction

The LUNGNOT04 cDNA library was constructed from lung tissue obtained from a 2-year-old male (specimen #RU95-09-0664; International Institute of Advanced Medicine, Exton Pa.) who died of anoxia.

The cells were lysed using a Brinkmann Homogenizer Polytron PT-3000 (Brinkmann Instruments, Westbury N.J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with phenol chloroform pH 4.0, precipitated using 0.3 M sodium acetate and 2.5 volumes of ethanol, resuspended in RNAse-free water and DNase treated at 37° C. The RNA was re-extracted with phenol chloroform pH 8.0 and precipitated using sodium acetate and ethanol as before. The mRNA was isolated using the Qiagen Oligotex kit (QIAGEN Inc, Chatworth Calif.) and used to construct the cDNA library.

The mRNA was handled according to the recommended protocols in the SuperScript Plasmid System for cDNA synthesis and cloning (Cat. #18248-013; Gibco/BRL, Gaitherburg Md.). cDNAs were fractionated on a Sepharose CL4B column (Cat. #275105; Pharmacia), and those cDNAs exceeding 400 bp were ligated into pSport I. The plasmid pSport I was subsequently transformed into DH5a™ competent cells (Cat. #18258-012; Gibco/BRL).

II Isolation and Sequencing of cDNA Clones

Plasmid DNA was released from the cells and purified using the REAL Prep 96 plasmid kit (Cat. #26173; QIAGEN Inc). This kit enables alkaline lysis and simultaneous purification of 96 samples in a 96-well block using multichannel reagent dispensers. The recommended protocol was employed except for the following changes: 1) the bacteria were cultured in 1 ml of sterile Terrific Broth (Cat. #22711, Gibco/BRL) with carbenicillin at 25 mg/L and glycerol at 0.4%; 2) the cultures were incubated for 19 hours after the wells were inoculated and then lysed with 0.3 ml of lysis buffer; 3) following isopropanol precipitation, the plasmid DNA pellet was resuspended in 0.1 ml of distilled water. After the final step in the protocol, samples were transferred to a Beckman 96-well block for storage.

The cDNAs were sequenced by the method of Sanger F and A R Coulson (1975; J Mol Biol 94:441f), using a Hamilton Micro Lab 2200 (Hamilton, Reno Nev.) in combination with Peltier Thermal Cyclers (PTC200 from M J Research, Watertown Mass.) and Applied Biosystems 377 DNA Sequencing Systems; and the reading frame was determined.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc. Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Extension of PDIH to Full Length or to Recover Regulatory Elements

The nucleic acid sequence of full length PDIH (SEQ ID NO:1) may be used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known PDIH sequence "outward" generating amplicons containing new, unknown nucleotide sequence for the region of interest. The initial primers may be designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original cDNA library may be used to extend the sequence, or a human genomic library is used to extend and amplify 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M J Research, Watertown Mass.) and the following parameters:

| Step | Conditions |
| --- | --- |
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 $\mu$l aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 $\mu$l of ligation buffer, 1 $\mu$l T4-DNA ligase (15 units) and 1 $\mu$l T4 polynucleotide kinase are added, and the mixture is incubated at room temperature for 2–3 hours or overnight at 16° C. Competent E. coli cells (in 40 $\mu$l of appropriate media) are transformed with 3 $\mu$l of ligation mixture and cultured in 80 $\mu$l of SOC medium (Sambrook J et al, supra). After Incubation for one hour at 37° C., the whole transformation mixture is plated on Luria Bertani (LB)-agar (Sambrook J et al, supra) containing 2×Carb. The following day, several colonies are randomly picked from each plate and cultured in 150 $\mu$l of liquid LB/2×Carb medium placed in an individual well of an appropriate, commercially-available, sterile 96-well microtiter plate. The following day, 5 $\mu$l of each overnight culture is transferred into a non-sterile 96-well plate and after dilution 1:10 with water, 5 $\mu$l of each sample is transferred into a PCR array.

For PCR amplification, 18 $\mu$l of concentrated PCR reaction mix (3.3×) containing 4 units of rTth DNA polymerase, a vector primer and one or both of the gene specific primers used for the extension reaction are added to each well.

Amplification is performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

V Labeling of Hybridization Probes

Hybridization probes derived from SEQ ID NO:1 may be employed to screen cDNAs, genomic DNAs or mRNAs. Although the labeling of oligonucleotides, consisting of about 20 base-pairs, is specifically described, essentially the same procedure may be used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynudeotide kinase (DuPont NEN®, Boston Mass.). The labeled oligonucleotides are purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonudeases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT ART™ film (Kodak, Rochester N.Y.) is exposed to the blots in a Phosphoimager cassette (Molecular Dynamics, Sunnyvale Calif.) for several hours, hybridization patterns are compared visually.

VI Antisense Molecules

The pdih sequence, or any part thereof, may be used to inhibit in vivo or in vitro expression of native pdih. Although use of antisense oligonucleotides, comprising about 20 base-pairs, is specifically described, essentially the same procedure may be used with larger cDNA fragments. An oligonucleotide based on the coding sequence of PDIH as shown in FIGS. 1A, 1B, 1C, and 1D may be used to inhibit expression of native PDIH. The complementary oligonucleotide can be designed from the most unique 5' sequence as shown in FIGS. 1A, 1B, 1C, and 1D and used either to inhibit transcription by preventing promoter binding to the upstream nontranslated sequence or translation of a pdih transcript by preventing the ribosome from binding. Using an appropriate portion of the leader and 5' sequence of SEQ ID NO:1, an effective antisense oligonucleotide would include any 15–20 nucleotides spanning the region which translates into the signal or early coding sequence of the polypeptide as shown in FIGS. 1A, 1B, 1C, and 1D.

VII Expression of PDIH

Expression of the PDIH may be accomplished by subcloning the cDNAs into appropriate vectors and transfecting the vectors into host cells. In this case, the cloning vector, pSport, previously used for the generation of the cDNA library is used to express PDIH in E. coli. Upstream of the cloning site, this vector contains a promoter for $\beta$-galactosidase, followed by sequence containing the amino-terminal Met and the subsequent 7 residues of $\beta$-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of $\beta$-galactosidase, about 5 to 15 residues of linker, and the full length PDIH. The signal sequence directs the secretion of PDIH Into the bacterial growth media which can be used directly in the following assay for activity.

VIII PDIH Activity

The activity of purified PDIH can be tested by introducing the molecule into an in vitro production system for tPA. If the current production systems produced a yield of 20%, then any statistically significant improvement of correctly folded tPA above 20% would indicate that PDIH is active and functioning correctly.

IX Production of PDIH Specific Antibodies

Although PDIH purified using PAGE electrophoresis (Maniatis, supra) can be used to immunize rabbits using standard protocols, a monoclonal approach is more commonly employed. The amino acid sequence translated from PDIH is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel F M et al (supra) and shown in FIGS. 4, 6, and 8.

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

X Purification of Native PDIH Using Specific Antibodies

Native or recombinant PDIH can be purified by immunoaffinity chromatography using antibodies specific for PDIH. An immunoaffinity column is constructed by covalently coupling PDIH antibody to an activated chromatographic resin such as CnBr-activated Sepharose (Pharmacia Biotech). After the coupling, the resin is blocked and washed according to the manufacturer's instructions.

Media containing PDIH is passed over the immunoaffinity column, and the column is washed under conditions that allow the preferential absorbance of PDIH (eg, high ionic strength buffers in the presence of detergent). The column is eluted under conditions that disrupt antibody/PDIH binding (eg, a buffer of pH 2–3 or a high concentration of a chaotrope such as urea or thiocyanate ion), and PDIH is collected.

XI Identification of Molecules Which Interact with PDIH

PDIH, or biologically active fragments thereof, are labelled with $^{125}$I Bolton-Hunter reagent (Bolton, A E and Hunter, W M (1973) Biochem J 133: 529). Candidate molecules previously arrayed in the wells of a 96 well plate are incubated with the labelled PDIH, washed and any wells with labelled PDIH complex are assayed. Data obtained using different concentrations of PDIH are used to calculate values for the number, affinity, and association of PDIH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
       (A) LENGTH: 1493 base pairs
       (B) TYPE: nucleic acid
       (C) STRANDEDNESS: single
       (D) TOPOLOGY: linear (ii) MOLECULE TYPE: cDNA (vii) IMMEDIATE SOURCE:
       (A) LIBRARY: LUNGNOT04
       (B) CLONE: 890200

(xi) SEQUENCE DESCRIPTION: SEQ ID NO:1:

```
AGGTGCCGCT GCCTGGAGAA TCCTCCGCTG CCGTCGNTCC CGGAGCCAGC CCTTTCCTAA      60

CCCAACCCAA NCCAGCCCAG TCCCAGCCGC NAGCGCCTGT CCCTGTCACG GACCCCAGCG     120

TTACCATGCA TCCTGCCGTC TTCCTATCCT TACCCGACCT CAGATGCTCC CTTCTGCTCC     180

TGGTAACTTG GGTTTTTACT CCTGTAACAA CTGAAATAAC AAGTCTTGCT ACAGAGAATA     240

TAGATGAAAT TTTAAACAAT GCTGATGTTG CTTTAGTAAA TTTTTATGCT GACTGGTGTC     300

GTTTCAGTCA GATGTTGCAT CCAATTTTTG AGGAAGCTTC CGATGTCATT AAGGAAGAAT     360

TTCCAAATGA AAATCAAGTA GTGTTTGCCA GAGTTGATTG TGATCAGCAC TCTGACATAG     420

CCCAGAGATA CAGGATAAGC AAATACCCAA CCCTCAAATT GTTTCGTAAT GGGATGATGA     480

TGAAGAGAGA ATACAGGGGT CAGCGATCAG TGAAAGCATT GGCAGATTAC ATCAGGCAAC     540

AAAAAAGTGA CCCCATTCAA GAAATHCGGG ACTTAGCAGA AATCACCACT CTTGATCGCA     600

GCAAAAGAAA TATCATTGGA TATTTKGAGC AAAAGGACTC GGACAACTAT AGAGTTTTTG     660

AACGAGTAGC GAATATTTTG CATGATGACT GTGCCTTTCT TTCTGCATTT GGGGATGTTT     720

CAAAACCGGA AAGATATAGT GGCGACAACA TAATCTACAA ACCACCAGGG CATTCTGCTC     780

CGGATATGGT GTACTTGGGA GCTATGACAA ATTTTGATGT GACTTACAAT TGGATTCAAG     840

ATAAATGTGT TCCTCTTGTC CGAGAAATAA CATTTGAAAA TGGAGAGGAA TTGACAGAAG     900

AAGGACTGCC TTTTCTCATA CTCTTTCACA TGAAAGAAGA TACAGAAAGT TTAGAAATAT     960

TCCAGAATGA AGTAGCTCGG CAATTAATAA GTGAAAAAGG TACAATAAAC TTTTTACATG    1020

CCGATTGTGA CAAATTTAGA CATCCTCTTC TGCACATACA GAAAACTCCA GCAGATTGTC    1080

CTGTAATCGC TATTGACAGC TTTAGGCATA TGTATGTGTT TGGAGACTTC AAAGATGTAT    1140

TAATTCCTGG AAAACTCAAG CAATTCGTAT TTGACTTACA TTCTGGAAAA CTGCACAGAG    1200

AATTCCATCA TGGACCTGAC CCAACTGATA CAGCCCCAGG AGAGCAAGCC CAAGATGTAG    1260

CAAGCAGTCC ACCTGAGAGC TCCTTCCAGA AACTAGCACC CAGTGAATAT AGGTATACTC    1320

TATTGAGGGA TCGAGATGAG CTTTAAAAAC TTGAAAAACA GTTTGTAAGC CTTTCAACAG    1380
```

```
CAGCATCAAC CTACGTGGTG GAAATAGTAA ACCTATATTT TCATAATTCT ATGTGTATTT      1440

TTATTTTGAA TAAACAGAAA GAAATTTTGG GGTTTTATTT TTTTNTCCCC GGC            1493

(2) INFORMATION FOR SEQ ID NO:2:

(i) SEQUENCE CHARACTERISTICS:
         (A) LENGTH: 406 amino acids
         (B) TYPE: amino acid
         (C) STRANDEDNESS: single
         (D) TOPOLOGY: linear (ii) MOLECULE TYPE: peptide (vii) IMMEDIATE SOURCE:
         (A) LIBRARY: LUNGNOT04
         (B) CLONE: 809200

(xi) SEQUENCE DESCRIPTION: SEQ ID NO:2:
```

| Met | His | Pro | Ala | Val | Phe | Leu | Ser | Leu | Pro | Asp | Leu | Arg | Cys | Ser | Leu |
|-----|-----|-----|-----|-----|-----|-----|-----|-----|-----|-----|-----|-----|-----|-----|-----|
| 1 | | | | 5 | | | | | 10 | | | | | 15 | |

Leu Leu Leu Val Thr Trp Val Phe Thr Pro Val Thr Thr Glu Ile Thr
                20                  25                  30

Ser Leu Ala Thr Glu Asn Ile Asp Glu Ile Leu Asn Asn Ala Asp Val
            35                  40                  45

Ala Leu Val Asn Phe Tyr Ala Asp Trp Cys Arg Phe Ser Gln Met Leu
    50                  55                  60

His Pro Ile Phe Glu Glu Ala Ser Asp Val Ile Lys Glu Glu Phe Pro
65                  70                  75                  80

Asn Glu Asn Gln Val Val Phe Ala Arg Val Asp Cys Asp Gln His Ser
                85                  90                  95

Asp Ile Ala Gln Arg Tyr Arg Ile Ser Lys Tyr Pro Thr Leu Lys Leu
            100                 105                 110

Phe Arg Asn Gly Met Met Met Lys Arg Glu Tyr Arg Gly Gln Arg Ser
        115                 120                 125

Val Lys Ala Leu Ala Asp Tyr Ile Arg Gln Gln Lys Ser Asp Pro Ile
130                 135                 140

Gln Glu Ile Arg Asp Leu Ala Glu Ile Thr Thr Leu Asp Arg Ser Lys
145                 150                 155                 160

Arg Asn Ile Ile Gly Tyr Xaa Glu Gln Lys Asp Ser Asp Asn Tyr Arg
                165                 170                 175

Val Phe Glu Arg Val Ala Asn Ile Leu His Asp Asp Cys Ala Phe Leu
            180                 185                 190

Ser Ala Phe Gly Asp Val Ser Lys Pro Glu Arg Tyr Ser Gly Asp Asn
        195                 200                 205

Ile Ile Tyr Lys Pro Pro Gly His Ser Ala Pro Asp Met Val Tyr Leu
210                 215                 220

Gly Ala Met Thr Asn Phe Asp Val Thr Tyr Asn Trp Ile Gln Asp Lys
225                 230                 235                 240

Cys Val Pro Leu Val Arg Glu Ile Thr Phe Glu Asn Gly Glu Glu Leu
                245                 250                 255

Thr Glu Glu Gly Leu Pro Phe Leu Ile Leu Phe His Met Lys Glu Asp
            260                 265                 270

Thr Glu Ser Leu Glu Ile Phe Gln Asn Glu Val Ala Arg Gln Leu Ile
        275                 280                 285

Ser Glu Lys Gly Thr Ile Asn Phe Leu His Ala Asp Cys Asp Lys Phe
290                 295                 300

Arg His Pro Leu Leu His Ile Gln Lys Thr Pro Ala Asp Cys Pro Val

```
          305                 310                 315                 320
Ile Ala Ile Asp Ser Phe Arg His Met Tyr Val Phe Gly Asp Phe Lys
                325                 330                 335

Asp Val Leu Ile Pro Gly Lys Leu Lys Gln Phe Val Phe Asp Leu His
                340                 345                 350

Ser Gly Lys Leu His Arg Glu Phe His His Gly Pro Asp Pro Thr Asp
                355                 360                 365

Thr Ala Pro Gly Glu Gln Ala Gln Asp Val Ala Ser Ser Pro Pro Glu
                370                 375                 380

Ser Ser Phe Gln Lys Leu Ala Pro Ser Glu Tyr Arg Tyr Thr Leu Leu
385                 390                 395                 400

Arg Asp Arg Asp Glu Leu
                405
```

(2) INFORMATION FOR SEQ ID NO:3:

(i) SEQUENCE CHARACTERISTICS:
        (A) LENGTH: 389 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: GI 1086627

(xi) SEQUENCE DESCRIPTION: SEQ ID NO:3:

```
Met Phe His Glu Met Phe Phe Tyr Lys Lys Asn Gln Lys Thr Asp Leu
1                   5                  10                  15

Lys Lys Leu Val Val Phe Val Ala Phe Cys Ala Asp Trp Cys Pro Phe
                20                  25                  30

Ser Arg Arg Leu Lys Pro Ile Phe Glu Glu Ser Ala Arg Val Phe His
                35                  40                  45

Gln Glu Asn Pro Gln Ala Ser Ala Val Trp Ala Ile Val Asp Ser Gln
50                  55                  60

Arg Gln Ala Asp Ile Gly Asp Lys Tyr Phe Val Asn Lys Tyr Pro Thr
65                  70                  75                  80

Met Lys Val Phe Val Asn Gly Glu Leu Ile Thr Lys Glu Tyr Arg Ser
                85                  90                  95

Thr Arg Ser Val Glu Ala Leu Thr Asn Phe Val Lys Phe Gln Leu Ser
                100                 105                 110

Thr Ala Ile Asn Glu Phe Ser Ser Gln Asp Gln Leu Asn Gln Glu Met
                115                 120                 125

Asp Lys Ser Lys Arg Asn Val Val Ala Trp Leu Lys Lys Asp Gly Pro
                130                 135                 140

Glu Phe Ala Asn Leu Lys Lys Val Ala Ser Ile Leu Arg Glu Asp Cys
145                 150                 155                 160

Ser Phe Trp Val Pro Thr Asp His Phe Gly Thr Gln Thr Asn Asp Asn
                165                 170                 175

Lys Leu Ser Phe Phe Asp Pro Asp Ser Asn Glu Glu Ala Lys Phe Thr
                180                 185                 190

Gly Asn Phe Asn Asp Tyr Asp Phe Val Lys Gln Trp Val Thr Asp Lys
                195                 200                 205

Cys Ile Pro Leu Val Arg Glu Val Thr Phe Glu Asn Val Glu Glu Leu
                210                 215                 220

Thr Glu Glu Gly Met Pro Phe Leu Ile Tyr Phe Arg Asp Pro Asp Asn
```

-continued

```
                225                 230                 235                 240
Lys Thr Thr Asp Lys Val Phe Gly Glu Ala Val Ala Arg Glu Leu Tyr
                    245                 250                 255

Asp Gln Arg Ser Ala Ile Asn Pro Leu Leu Ala Asp Gly His Lys Phe
                260                 265                 270

Ala His Pro Leu Lys His Leu Gly Lys Thr Lys Glu Asp Leu Pro Val
                275                 280                 285

Leu Ala Ile Asp Ser Phe Gln His Met Tyr Leu Phe Pro Asp Met Thr
                290                 295                 300

Gln Met Asn Ile Pro Gly Lys Leu Arg Glu Phe Val Met Asp Leu His
305                 310                 315                 320

Ser Gly Lys Leu His Lys Asp Phe His Glu Asn Leu Asp Gln Arg Met
                325                 330                 335

Ile Glu Leu Ala Lys Ala Lys Ala Ala Arg Gly Ile Thr Asp Asp His
                340                 345                 350

Glu Ala Gln Ala Pro Ser Thr Arg Pro Ile Asp Thr Thr Pro Pro Pro
                355                 360                 365

Ser Val Phe Lys Glu Leu Lys Pro Ser Asp Lys Arg Tyr Ser Ile Leu
                370                 375                 380

Gln Lys Ser Glu Leu
385

(2) INFORMATION FOR SEQ ID NO:4:

(i) SEQUENCE CHARACTERISTICS:
        (A) LENGTH: 364 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: GI 729442

(xi) SEQUENCE DESCRIPTION: SEQ ID NO:4:

Met Lys Met Glu Met His Gln Ile Trp Ser Arg Ile Ala Leu Ala Ser
1               5                   10                  15

Phe Ala Phe Ala Ile Leu Phe Val Ser Val Ser Ala Asp Val Val
                20                  25                  30

Val Leu Thr Glu Glu Asn Phe Glu Lys Glu Val Gly His Asp Lys Gly
                35                  40                  45

Ala Leu Val Glu Phe Tyr Ala Pro Trp Cys Gly His Cys Lys Lys Leu
            50                  55                  60

Ala Pro Glu Tyr Glu Lys Leu Pro Asn Ser Phe Lys Lys Ala Lys Ser
65                  70                  75                  80

Val Leu Ile Ala Lys Val Asp Cys Asp Glu His Lys Ser Val Cys Ser
                85                  90                  95

Lys Tyr Gly Val Ser Gly Tyr Pro Thr Ile Gln Trp Phe Pro Lys Gly
                100                 105                 110

Ser Leu Glu Pro Lys Lys Phe Glu Gly Pro Arg Thr Ala Glu Ser Leu
                115                 120                 125

Ala Glu Phe Val Asn Thr Glu Gly Gly Thr Asn Val Lys Ile Ala Thr
                130                 135                 140

Ala Pro Ser His Val Val Val Leu Thr Pro Glu Thr Phe Asn Glu Val
145                 150                 155                 160

Val Leu Asp Gly Thr Lys Asp Val Leu Val Glu Phe Tyr Ala Pro Trp
```

```
                          165                 170                 175
Cys Gly His Cys Lys Ser Leu Ala Pro Ile Tyr Glu Lys Val Ala Ala
            180                 185                 190
Val Phe Lys Ser Glu Asp Val Val Ile Ala Asn Leu Asp Ala Asp
        195                 200                 205
Lys Tyr Arg Asp Leu Ala Glu Lys Tyr Asp Val Ser Gly Phe Pro Thr
    210                 215                 220
Leu Lys Phe Phe Pro Lys Gly Asn Lys Ala Gly Glu Asp Tyr Gly Gly
225                 230                 235                 240
Gly Arg Asp Leu Asp Asp Phe Val Ala Phe Ile Asn Glu Lys Ser Gly
            245                 250                 255
Thr Ser Arg Asp Ala Lys Gly Gln Leu Thr Ser Glu Ala Gly Ile Val
        260                 265                 270
Glu Asp Leu Asp Glu Leu Val Lys Glu Phe Val Ala Ala Asn Asp Glu
    275                 280                 285
Glu Lys Lys Ala Val Phe Ala Arg Ile Glu Glu Val Lys Lys Leu
290                 295                 300
Glu Gly Ser Ala Ser Arg Tyr Gly Lys Ile Tyr Leu Lys Val Ser Lys
305                 310                 315                 320
Lys Tyr Leu Glu Lys Gly Ser Asp Tyr Ala Lys Asn Glu Ile Gln Arg
            325                 330                 335
Leu Glu Arg Leu Leu Glu Lys Ser Ile Ser Pro Ala Lys Ala Asp Glu
            340                 345                 350
Leu Thr Leu Lys Lys Asn Ile Leu Ser Thr Tyr Ala
            355                 360
```

(2) INFORMATION FOR SEQ ID NO:5:

(i) SEQUENCE CHARACTERISTICS:
        (A) LENGTH: 251 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: HMC1N0T01
        (B) CLONE: 008697

(xi) SEQUENCE DESCRIPTION: SEQ ID NO:5:

```
CAGAAGAAGG ACTGCCTTTN CTCATACTCT TTCACATGAA AGAAGATACA GAAAGTTTAG      60

AAATATTCCA GAATGAAGTA GCTCGGCAAT TAATAAGTGA AAAAGGTACA ATAAACTTTT     120

TACATGCCGA TTGTGACAAA TTTAGACATC CTCTTCTGCA CATACAGAAA ACTCCAGCAG     180

ATTGTCCTGT AATCGCTATT GACAGCTTTA GGCATATGTA TGTGTTTGGG GACTTCAAAG     240

ATGTATTAAT G                                                          251
```

(2) INFORMATION FOR SEQ ID NO:6:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: THP1N0B01
        (B) CLONE: 032387

(xi) SEQUENCE DESCRIPTION: SEQ ID NO:6:

```
GGACCTGACC CAACTNATAC AGCCCCAGGN GAGCAAGCCC AAGATGTAGC AAGCAGTCCA      60

CCTGANAGCT CCTTCCAGAA ACTNGCACCC AGTGAATATA GGTATACTCT ATTGAGGGAT     120

CGANATGAGC TTTAAAAACT TNAAAAACAG TTTNTAAGCC TTTNAACAGC AGNATCAACC     180

TACGTGGTGG NAATAGTAAA CCTNTATTTT NATAATTTTA TGGGTAATTT TTATTTTGNA     240

TAAACAGGAA GGAATTTTGG GGTTTTANTN TTTTTTNTCC CCGGC                    285
```

(2) INFORMATION FOR SEQ ID NO:7:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: FIBRNOT01
        (B) CLONE: 053124

(xi) SEQUENCE DESCRIPTION: SEQ ID NO:7:

```
CCAGGGCATT CTGCTCCGGA TATGGTGTAC TTGGGAGCTA TGACAAATTT TGATGTGACT      60

TACAATTGGA TTCAAGATAA ATGTGTTCCT CTTGTCCGAG AAATAACATT TGAAAATGGA     120

GAGGAATTGA CAGAAGAAGG ACTGCCTTTT CTCAT                               155
```

(2) INFORMATION FOR SEQ ID NO:8:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: EOS1HET02
        (B) CLONE: 285763

(xi) SEQUENCE DESCRIPTION: SEQ ID NO:8:

```
GAGAAATAAC ATTTGAAAAT GGAGAGGAAT TGACAGAAGA AGGACTGCCT TTNNTNATAC      60

TCTTTCACAT GAAAGAAGAT ACAGAAAGTT TAGAAATATT CCAGAATGAA GTAGCTCGGC     120

AATTAATAAG TGAAAAAGGT ACAATAAACT TTTTACATGC CGATTGTGAC AAATTTAGAC     180

ATCCTCTTCT GCACATACAG AAAACTCCAG CAGATTGTCC TGTAATCGCT ATTGACAGCT     240

TTAGGCATAT GTNTGTNTTT GGNGACTTCA AAGATGTATT AATTCCTGGA AAACTCAAGC     300

AATTCGTATT TGACTTACAT TCTGT                                          325
```

(2) INFORMATION FOR SEQ ID NO:9:

(i) SEQUENCE CHARACTERISTICS:
        (A) LENGTH: 143 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: TMLR3DT01
        (B) CLONE: 291250

(xi) SEQUENCE DESCRIPTION: SEQ ID NO:9:

```
AATNAGCTTT AAAAACTTGC AAAAACAGTT TGTAAGNCTT TNANCAGNAG CATCAACCNA      60

CGTGGTGGAA ATAGTAAACC TATATTTNNA TAATNCTATG TGTATTTTTA TTTTGAATAA     120

ACAGGGGAA NTTTTGGGTT TTT                                             143

(2) INFORMATION FOR SEQ ID NO:10:

(i) SEQUENCE CHARACTERISTICS:
        (A) LENGTH: 149 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: TMLR3DT01
        (B) CLONE: 292789

(xi) SEQUENCE DESCRIPTION: SEQ ID NO:10:

AATGGGCCTT TAAAAACTTG NAAAAACAGT TTGTAAGCCT TTCAACAGCA GCATCAACCT      60

ACGTGGTGGA AATAGTAAAC CTATATTTTC ATAATTCTAT GTGTATTTTT ATTTTGAATA     120

AACAGAAAGA AATTTTGGGT TTTTTTTTT                                      149

(2) INFORMATION FOR SEQ ID NO:11:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: EOS1HET02
        (B) CLONE: 318606

(xi) SEQUENCE DESCRIPTION: SEQ ID NO:11:

CCACGCAGCT GNCACAGAGN AATTCCATCA TGGACCTGAC CCAACTGGAT ACAGCCCCAG      60

GAGAGCAAGC CCAAGATGTA GCAAGCAGTC CACCTGAGAG CTCCTTCCAG AAACTAGCAC     120

CCAGTGAATA TAGGTATACT CTATTGAGGG ATCGAGATGA GCTTTAAAAA CTTNAAAAAC     180

AGTTTGTAAG CCTTTCAACA GCAGCATCAA CCTACGTGGT GGAAATAGTA AACCTATATT     240

TTCATAATTC TATGTGGATT TTATTTTGA ATAAACAGGA                            280

(2) INFORMATION FOR SEQ ID NO:12:

(i) SEQUENCE CHARACTERISTICS:
        (A) LENGTH: 394 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LVENNOT01
        (B) CLONE: 350290

(xi) SEQUENCE DESCRIPTION: SEQ ID NO:12:

CTATAGAGTT TTTGAACGAG TAGCGAATAT TTTGCATGAT GACTGTNCCT TTCTTTCTGC      60

ATTTGGGGAT GTTTCAAAAC CGGAAAGATA TAGTGGCGGC AACATAATCT ACAAACCACC     120

AGGGCATTCT GCTCCGGATA TGGTGTACTT GGGAGCTATG ACAAATTTTG ATGTGACTTA     180
```

```
CAATTGGATT CAAGATAAAT GTGTTCCTCT TGTCCGAGGA ATAACATTTG AAAATGGAGA      240

GGAATTGACA GAAGNAGGAC TGCCTTTNCT CATACTCTTT CACATGAAAG ANGTTNCAGA      300

AAGTTTAGGA ATATTCCAGA ATGANGAAGC TCGGCAATTA ATAGGNGAAA AAGGTCCAAT      360

AACCTTTTTA CATNCCGNTT TGNCAATTTA GACA                                 394

(2) INFORMATION FOR SEQ ID NO:13:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: SYNORAT01
        (B) CLONE: 365690

(xi) SEQUENCE DESCRIPTION: SEQ ID NO:13:

CAGAAGAAGG ACTGCCTTTT CTCATACTCT TTCACATGNA AGAAGATACA GAAAGTTTAG      60

AAATATTCCA GAATGAAGTA GCTCGGCAAT TAATAAGTGA AAAAGGTACA ATAAACTTTT     120

TACATGCCGA TTGTGACAAA TTTAGACATC CTCTTCTGCA CATACAGAAA ACTCCAGCAG     180

ATTGTCCTGT AATCGCTATT GACAGCTTTA GGCATATGTA TGTGTTTGGA GACTTCAAAG     240

ATGTATTAAT TCCTGG                                                     256

(2) INFORMATION FOR SEQ ID NO:14:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: EOSIHET02
        (B) CLONE: 406416

(xi) SEQUENCE DESCRIPTION: SEQ ID NO:14:

GCAATTCGTA TTTGACTTAC ATTCTGGAAA ACTGCACAGA GAATTCCATC ATGGACCTGA      60

CCCAACTGAT ACAGCCCCAG GAGAGCAAGC CCAAGATGTA GCAAGCAGTC CACCTGAGAG     120

CTCCTTCCAG AAACTAGCAC CCAGTGAATA TAGGTATACT CTATTGAGGG ATCGAGATGA     180

GCTTTAAAAA CTTGAAAAAC AGTTTGTAAG CCTTTCAACA GCAGCAT                   227

(2) INFORMATION FOR SEQ ID NO:15:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: MMLR2DT01
        (B) CLONE: 478027

(xi) SEQUENCE DESCRIPTION: SEQ ID NO:15:

CTCTTTCACA TGAAAGAAGA TACAGAAAGT TTAGAAATAT TCCAGAATGA AGTAGCTCGG      60

CAATTAATAA GTGAAAAAGG TACAATAAAC TTTTTACATG CCGATTGTGA CAAATTTAGA     120
```

```
CATCCTCTTC TGCACATACA GAAAACTCCA GCAGATTGTC CTGTAATCGC TATTGACAGC        180

TTTAGGCATA TGTATGTGTT TGGAGACTTC AAAGATGTAT TAATTCCTGG NAAACTCAAG        240

CAATTCGTAT TTGACTTACA TTCTGGAAAA CTGCACAGG                               279

(2) INFORMATION FOR SEQ ID NO:16:

(i) SEQUENCE CHARACTERISTICS:
         (A) LENGTH: 281 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (A) LIBRARY: MMLR2DT01
         (B) CLONE: 478085

(xi) SEQUENCE DESCRIPTION: SEQ ID NO:16:

GAAAAGGTA CAATAAACTT TTTACATGCC GATTGTGACA AATTTAGACA TCCTCTTCTG         60

CACATACAGA AAACTCCAGC AGATTGTCCT GTAATCGCTA TTGACAGCTT TAGGCATATG        120

TATGTGTTTG GAGACTTCAA AGATGTATTA ATTCCTGGGA AACTCAAGCA ATTCGTATTT        180

GACTTACATT CTGGAAAACT GCACAGAGAA TTCCATCATG GACCTGACCC AACTGATACA        240

GCCCCAGGAG AGCAAGCCCA AGATGTAGCA AGCAGTCCAC C                           281

(2) INFORMATION FOR SEQ ID NO:17:

(i) SEQUENCE CHARACTERISTICS:
         (A) LENGTH: 92 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (A) LIBRARY: MMLR2DT01
         (B) CLONE: 521643

(xi) SEQUENCE DESCRIPTION: SEQ ID NO:17:

AACAGCAGCA TCAACCTACG TGGTGGAAAT AGTAAACCTA TATTTTCATA ATTCTATGTG        60

TATTTTTATT TTGAATAAAC AGAAAGAAAT TT                                     92

(2) INFORMATION FOR SEQ ID NO:18:

(i) SEQUENCE CHARACTERISTICS:
         (A) LENGTH: 297 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (A) LIBRARY: BRAINOT03
         (B) CLONE: 533824

(xi) SEQUENCE DESCRIPTION: SEQ ID NO:18:

CTTTCTGCAT TGGGGATGT TTCAAAACCG GAAAGATATA GTGGCGACAA CATAATCTAC         60

AAACCACCAG GGCATTCTGC TCCGGATATG GTGTACTTGG GAGCTATGAC AAATTTTGAT        120

GTGACTTACA ATTGGATTCA AGATAAATGT GTTCCTCTTA TCCGAGAAAT AACATTTGAA        180

ANTGGAGAGG AATTGACAGA AGAAGGACTG CCTTTTCTNA TACTCTNTCA CATGAAAGAA        240
```

```
GATACAGAAA GTTTAGAAAT ATTCCAGANT GAAGTAGCTC GGCAATTAAT AAGTGAG        297

(2) INFORMATION FOR SEQ ID NO:19:

(i) SEQUENCE CHARACTERISTICS:
          (A) LENGTH: 139 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (A) LIBRARY: OVARNOT02
          (B) CLONE: 545675

(xi) SEQUENCE DESCRIPTION: SEQ ID NO:19:

AAATTTAGAC ATCCTNTTCT GCACATACAG AAAACTCCAG CAGATTGTCC TGTAATCGCT     60

ATTGACAGCT TTAGGCATAT GTATGTGTTT GGAGACTTCA AGATGTATT AATTCCTGGN      120

AAACTCAAGC AATTCGTAT                                                  139

(2) INFORMATION FOR SEQ ID NO:20:

(i) SEQUENCE CHARACTERISTICS:
          (A) LENGTH: 160 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (A) LIBRARY: NEUTLPT01
          (B) CLONE: 564725

(xi) SEQUENCE DESCRIPTION: SEQ ID NO:20:

TATAGGTATA CTCTATTGAG GGATCGAGAT GAGCTTTAAA AACTTGAAAA ACAGTTTGTA     60

AGCCTTTCAA CAGCAGCATC AACCTACGTG GTGGAAATAG TAAACCTATA TTTTCATAAT     120

TCTATGTGTA TTTTTATTTT GAATAAACAG AAAGAAATTT                           160

(2) INFORMATION FOR SEQ ID NO:21:

(i) SEQUENCE CHARACTERISTICS:
          (A) LENGTH: 215 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (A) LIBRARY: UTRSNOT01
          (B) CLONE: 587535

(xi) SEQUENCE DESCRIPTION: SEQ ID NO:21:

CCAAGATGTA GCAAGCAGTC CACCTGAGAG CTCCTTCCAG AAACTAGCAC CCAGTGAATA     60

TAGGTATACT CTATTGAGGG ATCGAGATGA GCTTTAAAAA CTTGAAAAAC AGTTTGTAAG     120

CCTTTNAACA GCAGCATCAA CCTACGTGGT GGAAATAGTA AACCTATATT TTCATAATTC     180

TATGTGTATT TTTATTTTGA ATAAACAGAA AGNAA                                215

(2) INFORMATION FOR SEQ ID NO:22:

(i) SEQUENCE CHARACTERISTICS:
          (A) LENGTH: 236 base pairs
          (B) TYPE: nucleic acid
          (C) STRANDEDNESS: single
```

(D) TOPOLOGY: linear (ii) MOLECULE TYPE: cDNA (vii) IMMEDIATE SOURCE:
        (A) LIBRARY: UTRSNOT01
        (B) CLONE: 591297

(xi) SEQUENCE DESCRIPTION: SEQ ID NO:22:

ATTTGAAAAT GGAGAGGAAT TGACAGAAGA AGGACTGCCT TTNCTCATAC TCTTTCACAT    60

GAAAGAAGNT ACAGAAAGTT TAGNAATATT CCAGAATGAA GTAGCTCGGC AATTAATAAG   120

TGAAAAGGT ACAATAAACT TTTTACATGC CGNTTGTGAC AAATTTAGNN ATNCTCTTNT   180

GCACATACAG GAAACTTCAG NAGNTTGTCC TGTAATNGNT ATTTACAGGT TTAGGG       236

(2) INFORMATION FOR SEQ ID NO:23:

(i) SEQUENCE CHARACTERISTICS:
        (A) LENGTH: 218 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: PROSTUT03
        (B) CLONE: 788789

(xi) SEQUENCE DESCRIPTION: SEQ ID NO:23:

ACATAATCTA CAAACCACCA GGGCATTCTG CTCCGGATAT GGTGTACTTG GGAGCTATGA    60

CAAATTTTGA TGTGACTTAC AATTGGATTC AAGATAAATG TGTTCCTCTT GTCCGAGAAA   120

TAACATTTGA AAATGGAGAG GAATTGACAG AAGAAGGACT GCCTTTTCTC ATACTCTTTC   180

ACATGAAAGA AGATACAGAA AGTTTAGAAA TATTCCAG                           218

(2) INFORMATION FOR SEQ ID NO:24:

(i) SEQUENCE CHARACTERISTICS:
        (A) LENGTH: 268 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LUNGNOT04
        (B) CLONE: 809200p (xi) SEQUENCE DESCRIPTION: SEQ ID NO:24:

GCAAAAGGAC TCGGACAACT ATAGAGTTTT TGAACGAGTA GCGAATATTT TGCATGATGA    60

CTGTGCCTTT CTTTCTGCAT TGGGGATGT TTCAAAACCG GAAAGATATA GTGGCGACAA   120

CATAATCTAC AAACCACCAG GGCATTCTGC TCCGGATATG GTGTACTTGG GAGCTATGAC   180

AAATTTTGAT GTGACTTACA ATTGGGNTCA AGNTAAATNT GTTCNCTTGT CCGAGANATA   240

ACATTGAAAA TGGAGAGGNN TTGACAGA                                     268

(2) INFORMATION FOR SEQ ID NO:25:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
    (A) LIBRARY: LUNGNOT04
    (B) CLONE: 812834

(xi) SEQUENCE DESCRIPTION: SEQ ID NO:25:

AGCAGATTGT CCTGTAATCG CTATTGACAG CTTTAGGCAT ATGTATGTGT TTGGAGACTT        60

CAAAGATGTA TTAATTCCTG GNAAACTCAA GCAATTCGTA TTTGACTTAC ATTCTGGAAA       120

ACTGCACAGA GGATTCCATC ATGGACCTGA CCCAACTGAT ACAGCCCCAG GAGAGCAAGC       180

CCAAGATGTA GCAAGCAGTC CACCTGAGAG CTTCTTNCAG AAACTAGCAC CCAGTGAATA       240

TAGGTATACT CTATTGAGGG TCGAGATGAG CTTTAAAAAC TTGNAAAACA                  290

(2) INFORMATION FOR SEQ ID NO:26:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: PROSNOT07
        (B) CLONE: 835802

(xi) SEQUENCE DESCRIPTION: SEQ ID NO:26:

TCTGCACATA CAGAAAACTC CAGCAGATTG TCCTGTAATC GCTATTGACA GCTTTAGGCA        60

TATGTATGTG TTTGGAGACT TCAAAGATGT ATTAATTCCT GGAAAACTCA AGCAATTCGT       120

ATTTGACTTA CATTCTGGAA AACTGCACAG AGAATTCCAT CATGGACCTG ACCCAACTGA       180

TACAGCCCCA GGAGAGCAAG CCCAAGATGT AGCAAGCAGT CCACCTGAGA GCTCCTTCCA       240

GAAACTAGCA CCCAGTGAAT ATAGGTATAC TCTATTGAGG G                          281

(2) INFORMATION FOR SEQ ID NO:27:

(i) SEQUENCE CHARACTERISTICS:
        (A) LENGTH: 263 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: THYRNOT02
        (B) CLONE: 881621

(xi) SEQUENCE DESCRIPTION: SEQ ID NO:27:

AAATATTCCA GAATGAAGTA GCTCGGCAAT TAATAAGTGA AAAAGGTACA ATAAACTTTT        60

TACATGCCGA TTGTGACAAA TTTAGACATC CTNTTCTGCA CATACAGAAA ACTCCAGCAG       120

ATTGTCCTGT AATCGCTATT GACAGCTTTA GGCATATGTA TGTGTTTGGA GACTTCAAAG       180

ATGTATTAAT TCCTGGAAAA CTCAAGCAAT TCGTATTTGA CTTACATTCT GGAAAACTGC       240

ACAGAGANTT CCATCATGGA CCT                                              263

(2) INFORMATION FOR SEQ ID NO:28:

(i) SEQUENCE CHARACTERISTICS:
        (A) LENGTH: 259 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
          (A) LIBRARY: THYRNOT02
          (B) CLONE: 882286

(xi) SEQUENCE DESCRIPTION: SEQ ID NO:28:

AAATATTCCA GAATGAAGTA GCTCGGCAAT TAATAAGTGA AAAAGGTACA ATAAACTTTT    60

TACATGCCGA TTGTGACAAA TTTAGACATC CTCTTCTGCA CATACAGAAA ACTCCAGCAG   120

ATTGTCCTGT AATCGCTATT GACAGCTTTA GGCATATGTA TGTGTTTGGA GACTTCAAAG   180

ATGTATTAAT TCCTGGNAAA CTCAAGCAAT TCGTATTTGA CTTACATTCT GGAAAACTGC   240

ACAGAGAATT CCATCATGG                                               259

(2) INFORMATION FOR SEQ ID NO:29:

(i) SEQUENCE CHARACTERISTICS:
          (A) LENGTH: 226 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (A) LIBRARY: THP1PLB01
          (B) CLONE: 014106

(xi) SEQUENCE DESCRIPTION: SEQ ID NO:29:

GTTGCATCCA ATTTTTGAGG AAGCTTCCGA TGTCATTAAG GAAGAATTTC CAAATGAAAA    60

TCAAGTAGTG TTTGCCAGAG TTGATTGTGA TCAGCACTCT GACATAGCCC AGAGATACAG   120

GATAAGCAAA TACCCAACCC TCAAATTGTT TCGTAATGGG ATGATGATGA AGAGAGAATA   180

CAGGGGTCAG CGATCAGTGA AAGCATTNGC AGATTACNTC AGGCAT                 226

(2) INFORMATION FOR SEQ ID NO:30:

(i) SEQUENCE CHARACTERISTICS:
          (A) LENGTH: 356 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (A) LIBRARY: HUVELPB01
          (B) CLONE: 019892

(xi) SEQUENCE DESCRIPTION: SEQ ID NO:30:

CAANAAAGTG ACCCCATTCA AGAAATCCGG GACTTAGCAG AAATCACCAC NCTNGANCGC    60

AGCAAANGNA ATATCATTGG ATATTTGGAG CAAAAGGACT CGGACANCTA NAGAGTTTTT   120

TNANCGAGTA GCGNATATTT GNCATGANNA CTGTCCCTNT CTTTNCTGCA TTNGGGGATN   180

TNTCAAAACC GNAAAGATAT AGTGGCGACA ACATAATCTT CANTCCNCCN NGGNATTCTT   240

TCTCCGGATA TTGTGTNCCT GGGTGCTATT NCANTTTGTG NTTGGTNTCT TTCATTNNTT   300

TTNATNTTTA TTTTGTTTCT TCTTTTCCGT GTTTTTNCAT TTTGTTTATT TTGTTG       356

(2) INFORMATION FOR SEQ ID NO:31:

(i) SEQUENCE CHARACTERISTICS:
          (A) LENGTH: 214 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
    (A) LIBRARY: SPINFET01
    (B) CLONE: 029425

(xi) SEQUENCE DESCRIPTION: SEQ ID NO:31:

| | | | | | |
|---|---|---|---|---|---|
| TCCAAATGAA | AATCAAGTAG | TGTTTGCCAG | AGTTGATTGT | GATCAGCACT | CTGACATAGC | 60 |
| CCAGAGATAC | AGGATANGCA | AATACCCAAC | CCTCAAATTG | TTTCGNAATG | GCGATNNTGA | 120 |
| TGAAGAGAGN | NTACAGGGGT | NAGGTGTNAC | ANGAGAAAGT | NTATACCNAG | GCCACCNGAT | 180 |
| ANCANCTTTC | CAAAAAGGNC | TNCGATACGG | GNTT | | | 214 |

(2) INFORMATION FOR SEQ ID NO:32:

(i) SEQUENCE CHARACTERISTICS:
      (A) LENGTH: 280 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: TLYMNOT02
      (B) CLONE: 450935

(xi) SEQUENCE DESCRIPTION: SEQ ID NO:32:

| | | | | | |
|---|---|---|---|---|---|
| GAAATTTTAA | ACAATGCTGA | TGTTGCTTTA | GTAAATTTTT | ATGCTGACTG | GTGTCGTTTC | 60 |
| AGTCAGATGT | TGCATCCAAT | TTTTGAGGAA | GCTTCCGATG | TCATTAAGGA | AGAATTTCCA | 120 |
| AATGAAAATC | AAGTAGTGTT | TGCCAGAGTT | GATTGTGATC | AGCACTCTGA | CATAGCCCAG | 180 |
| AGATACAGGA | TAAGCAAATA | CCCAACCCTC | AAATTGTTTC | GTAATGGGAT | GATGATGAAG | 240 |
| AGAGAATACA | GGGGTCAGCG | ATCAGTGAAA | GCATTGGCAG | | | 280 |

(2) INFORMATION FOR SEQ ID NO:33:

(i) SEQUENCE CHARACTERISTICS:
      (A) LENGTH: 267 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: KIDDNOT05
      (B) CLONE: 631328

(xi) SEQUENCE DESCRIPTION: SEQ ID NO:33:

| | | | | | |
|---|---|---|---|---|---|
| GGGATGATGA | TGAAGAGAGA | ATACAGGGGT | CAGCGATCAG | TGAAAGCATT | GGCAGATTAC | 60 |
| ATCAGGCAAC | AAAAAAGTGA | CCCCATTCAA | GAAATTCGGG | ACTTAGCAGA | AATCACCACT | 120 |
| CTTGATCGCA | GCAAAAGAAA | TATCATTGGN | TATTTTGAGC | AAAAGGACTC | GGACAACTAT | 180 |
| AGNGTTTTTG | AACGAGTAGC | GAATATTTTG | CATGATGACT | GTGCCTTTCT | TTCTGCATTT | 240 |
| GGGGTGTTTC | AAAACCGGGA | AGGTATT | | | | 267 |

(2) INFORMATION FOR SEQ ID NO:34:

(i) SEQUENCE CHARACTERISTICS:
      (A) LENGTH: 265 base pairs
      (B) TYPE: nucleic acid
      (C) STRANDEDNESS: single
      (D) TOPOLOGY: linear

```
        (ii) MOLECULE TYPE: cDNA (vii) IMMEDIATE SOURCE:
            (A) LIBRARY: BRSTNOT03
            (B) CLONE: 637955

(xi) SEQUENCE DESCRIPTION: SEQ ID NO:34:

TTTATGCTGA CTGGTGTCGT TTCAGTCAGA TGTTGCATCC AATTTTTGAG GAAGCTTCCG      60

ATGTCATTAA GGAAGAATTT CCAAATGAAA ATCAAGTAGT GTTTGCCAGA GTTGATTGTG     120

ATCAGCACTC TGACATAGCC CAGAGATACA GGATAAGCAA ATACCCAACC CTCAAATTGT     180

TTCGTAATGG GATGATGATG AAGAGAGAAT ACAGGGGTCA GCGATCAGTG AAAGCATTGG     240

CAGATTACAT CAGGCAACAA AAAAG                                           265

(2) INFORMATION FOR SEQ ID NO:35:

(i) SEQUENCE CHARACTERISTICS:
             (A) LENGTH: 420 base pairs
             (B) TYPE: nucleic acid
             (C) STRANDEDNESS: single
             (D) TOPOLOGY: linear (ii) MOLECULE TYPE: cDNA (vii) IMMEDIATE SOURCE:
             (A) LIBRARY: GenBank
             (B) CLONE: GI 1149007

(xi) SEQUENCE DESCRIPTION: SEQ ID NO:35:

AGGTGCCGCT GCCTGGAGAA TCCTCCGCTG CCGTCGNTCC CGGAGCCAGC CCTTTCCTAA      60

CCCAACCCAA NCCAGCCCAG TCCCAGCCGC NAGCGCCTGT CCCTGTCACG GACCCCAGCG     120

TTACCATGCA TCCTGCCGTC TTCCTATCCT TACCCGACCT CAGATGCTCC CTTCTGCTCC     180

TGGTAACTTG GGTTTTTACT CCTGTAACAA CTGAAATAAC AAGTCTTGCT ACAGAGAATA     240

TAGATGAAAT TTTAAACAAT GCTGATGTTG CTTTAGTAAA TTTTTATGCT GACTGGTGTC     300

GTTTCAGTCA GATGTTGCAT CCAATTTTTT GAGGAAGCTT CCGATGGTCA TTTAAGGAAG     360

GNATTTTCCA AAATGGAACA TCCAAGTTAG TGGTTTGCCC AAGAGTTGGA TNTGTGGAAT     420
```

We claim:

1. A purified polypeptide comprising the amino acid sequence of SEQ ID NO:2.

2. A process for producing therapeutic proteins wherein the purified polypeptide of claim 1 is added to the reaction mixture to improve the yield of biologically active recombinant protein.

* * * * *